United States Patent

Ohkawa et al.

[11] Patent Number: 5,837,438
[45] Date of Patent: Nov. 17, 1998

[54] SILVER HALIDE COLOR PHOTOGRAPHIC PHOTOSENSITIVE MATERIAL

[75] Inventors: Atsuhiro Ohkawa; Keiji Mihayashi, both of Minami-Ashigara, Japan

[73] Assignee: Fuji Photo Film, Co., Ltd., Kanagawa, Japan

[21] Appl. No.: 35,878

[22] Filed: Mar. 23, 1993

Related U.S. Application Data

[63] Continuation of Ser. No. 835,572, Feb. 14, 1992, abandoned.

[30] Foreign Application Priority Data

Feb. 15, 1991 [JP] Japan ................................ 3-43008

[51] Int. Cl.$^6$ .................................................. G03C 7/305
[52] U.S. Cl. .......................... 430/544; 430/543; 430/957
[58] Field of Search ................................ 430/544, 543, 430/957

[56] References Cited

U.S. PATENT DOCUMENTS

| 4,861,701 | 8/1989 | Burns et al. | 430/544 |
| 4,962,018 | 10/1990 | Szajewski et al. | 430/544 |
| 5,034,311 | 7/1991 | Slusarek et al. | 430/544 |
| 5,055,385 | 10/1991 | Slusarek et al. | 430/544 |
| 5,360,709 | 11/1994 | Ohkawa et al. | 430/544 |

FOREIGN PATENT DOCUMENTS

| 035453 | 2/1989 | European Pat. Off. |
| 0354532 | 2/1989 | European Pat. Off. |
| 0438129 | 7/1991 | European Pat. Off. |
| 0438148 | 7/1991 | European Pat. Off. |
| 438129 | 7/1991 | European Pat. Off. |
| 438148 | 7/1991 | European Pat. Off. |
| 60-218645 | 11/1985 | Japan . |

OTHER PUBLICATIONS

World Patents Index Latest Week 8550, Derwent Publications Ltd., London, GB; AN 85–313735 Abstract.

*Primary Examiner*—Richard L. Schilling
*Attorney, Agent, or Firm*—Sughrue, Mion, Zinn, MacPeak & Seas, PLLC

[57] ABSTRACT

A compound represented by the following general formula (I) is added to at least one layer of a silver halide photographic photosensitive material, thereby improving sharpness and graininess or decreasing a variation in photographic performance during storage after photography and before development:

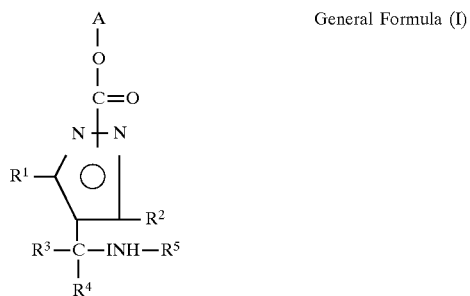

General Formula (I)

where A represents a coupler moiety, each of $R^1$ and $R^2$ independently represents a hydrogen atom or a substituent, each of $R^3$ and $R^4$ independently represents a hydrogen atom or an alkyl group, INH represents a group having a development inhibiting function, and $R^5$ represents a nonsubstituted phenyl group, a nonsubstituted primary alkyl group, or a primary alkyl group substituted with a group other than an aryl group, at least one of $R^1$ to $R^4$ being a substituent other than a hydrogen atom, and an —OC(=O)— group combining with one of two nitrogen atoms forming a pyrazole ring.

15 Claims, No Drawings

SILVER HALIDE COLOR PHOTOGRAPHIC PHOTOSENSITIVE MATERIAL

This is a continuation of application Ser. No. 07/835,572, filed Feb. 14, 1992, now abandoned.

BACKGROUND OF THE INVENTION

1. Field of the Invention

The present invention relates to a silver halide color photographic photosensitive material containing a novel compound which can release a development inhibitor at a proper timing during development.

2. Description of the Related Art

Recently, in the field of a silver halide photosensitive material, particularly a photographic color photosensitive material, a demand has arisen for a photosensitive material which has a high sensitivity, excellent graininess and sharpness, and a good storage stability, as represented by an IS)400 photosensitive material (Super HG-400: available from Fuji Photo Film Co., Ltd.) having a high image quality equivalent to ISO sensitivity 100.

As means for improving sharpness, JP-A-61-231553 or JP-A-61-240240 ("JP-A-" means Published Unexamined Japanese Patent Application), for example, discloses a coupler which causes a coupling reaction with an oxidation product of a developing agent, and then a cleavaged compound of which is oxidized by another molecule of the oxidation product of a developing agent, thereby releasing a development inhibitor having a timing group. However, these compounds have problems that, e.g., an improvement in sharpness is insufficient because the release rate of a development inhibitor is inappropriate, and a storage stability as a photosensitive material is unsatisfactory.

As a compound which can improve sharpness without deteriorating the storage stability of a photosensitive material, a compound which releases a development inhibitor imagewise through two or more timing groups is described in, e.g., JP-A-60-218645, JP-A-60-249148, JP-A-61-156127, and U.S. Pat. No. 4,861,701. These compounds, however, also have problems that improvements in sharpness and graininess are insufficient because the release rate (timing) of a development inhibitor is inadequate, the diffusibility of a development inhibitor is too large, or the diffusibility is too small due to a large molecular weight of the timing groups. In addition, many photosensitive materials containing these compounds introduce a large increase in fog or a large decrease in sensitivity when aged over extended periods after photography and before development or when stored at a high temperature and a high humidity.

SUMMARY OF THE INVENTION

It is, therefore, a first object of the present invention to provide a silver halide color photographic photosensitive material which has excellent sharpness and graininess and a small variation in photographic performance during storage after photography and before development.

It is a second object of the present invention to provide a silver halide color photographic photosensitive material whose development inhibitor release rate can be easily controlled.

The above objects of the present invention is achieved by a silver halide color photographic photosensitive material in which at least one silver halide emulsion layer is formed on a support, wherein said material contains a compound represented by general formula (I) below in at least one layer:

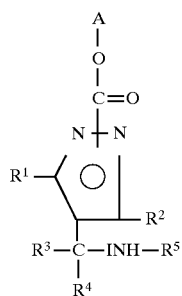

General Formula (I)

where A represents a coupler moiety, each of $R^1$ and $R^2$ independently represents a hydrogen atom or a substituent, each of $R^3$ and $R^4$ independently represents a hydrogen atom or an alkyl group, INH represents a group having a development inhibiting function, and $R^5$ represents a nonsubstituted phenyl group, a nonsubstituted primary alkyl group, or a primary alkyl group substituted with a group other than an aryl group, at least one of $R^1$ to $R^4$ being a substituent other than a hydrogen atom, and an —OC(=O)— group combining with one of two nitrogen atoms forming a pyrazole ring.

DETAILED DESCRIPTION OF THE PREFERRED EMBODIMENTS

A compound represented by general formula (I) will be described below.

In general formula (I), A represents a coupler moiety.

Examples of the coupler moiety represented by A are a yellow coupler moiety (e.g., an open-chain ketomethylene type coupler moiety such as acylacetanilide or malondianilide), a magenta coupler moiety (e.g., a coupler moiety of a 5-pyrazolone type, a pyrazolotriazole type, or an imidazopyrazole type), a cyan coupler moiety (e.g., a coupler moiety of a phenol type, a naphthol type, an imidazole type described in Unexamined Published European Patent Application No. 249,453, or a pyrazolopyrimidine type described in Published Unexamined European Patent Application No. 304,001), and a colorless compound forming coupler moiety (e.g., a coupler moiety of an indanone type or an acetophenone type). In addition, it is possible to use a heterocyclic coupler moiety described in U.S. Pat. Nos. 4,315,070, 4,183,752, 4,174,969, 3,961,959, or 4,171,223, or JP-A-52-82423.

A preferable example of A is a coupler moiety represented by the following general formula (Cp-1), (Cp-2), (Cp-3), (Cp-4), (Cp-5), (Cp-6), (Cp-7), (Cp-8), (Cp-9), (Cp-10), or (Cp-11). These couplers are preferable because of their higher coupling rates.

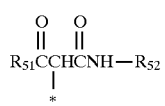

general formula (Cp-1)

general formula (Cp-2)

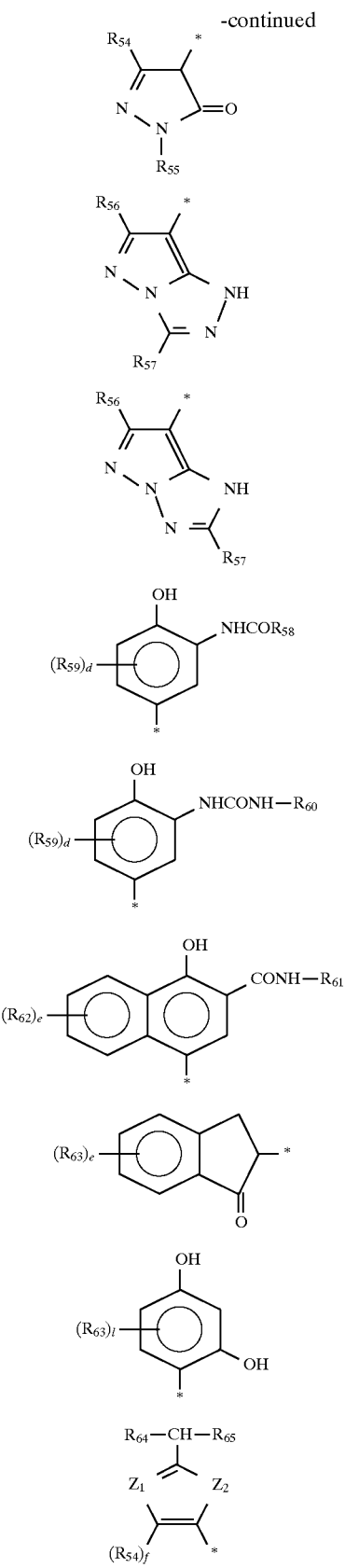

general formula (Cp-3)

general formula (Cp-4)

general formula (Cp-5)

general formula (Cp-6)

general formula (Cp-7)

general formula (Cp-8)

general formula (Cp-9)

general formula (Cp-10)

general formula (Cp-11)

In the above general formulas, symbol * represents a coupling position to be bonded to a group from —OCO— of general formula (I).

In the above general formulas, $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, $R_{63}$, $R_{64}$, or $R_{65}$ preferably contains a nondiffusing group. In that case, the group is selected such that the total number of carbon atoms is 8 to 40, and preferably 10 to 30. In the other cases, the total number of carbon atoms is pre- ferably 15 or less.

$R_{51}$ to $R_{65}$, l, d, e, and f will be described in detail below. In the following description, $R_{41}$ represents an aliphatic group, an aromatic group, or a heterocyclic group, $R_{42}$ represents an aromatic group or a heterocyclic group, and each of $R_{43}$, $R_{44}$, and $R_{45}$ independently represents a hydrogen atom, an aliphatic group, an aromatic group, or a heterocyclic group.

$R_{51}$ has the same meaning as $R_{41}$. Each of $R_{52}$ and $R_{53}$ has the same meaning as $R_{42}$. $R_{54}$ represents a group having the same meaning as $R_{41}$, an $R_{41}CON(R_{43})$-group, an $R_{41}R_{43}N$-group, an $R_{41}SO_2N(R_{43})$-group, an $R_{41}S$-group, an $R_{43}O$-group, an $R_{45}N(R_{43})CON(R_{44})$-group, or an N≡C-group. $R_{55}$ represents a group having the same meaning as $R_{41}$. Each of $R_{56}$ and $R_{57}$ independently represents a group having the same meaning as the $R_{43}$ group, an $R_{41}S$-group, an $R_{43}O$-group, an $R_{41}CON(R_{43})$-group, or an $R_{41}SO_2N(R_{43})$-group. $R_{58}$ represents a group having the same meaning as $R_{41}$. $R_{59}$ represents a group having the same meaning as $R_{41}$, an $R_{41}CON(R_{43})$-group, an $R_{41}OCON(R_{43})$-group, an $R_{41}SO_2N(R_{43})$-group, an $R_{43}R_{44}NCON(R_{45})$-group, an $R_{41}O$-group, an $R_{41}S$-group, a halogen atom, or an $R_{41}R_{43}N$-group. d represents 0, 1, 2, or 3. If d is a plural number, a plurality of $R_{59}$'s represent either the same substituent or different substituents. Alternatively, the respective $R_{59}$'s may couple with each other as divalent groups to form a cyclic structure. Examples of the cyclic structure are a pyridine ring and a pyrrole ring. $R_{60}$ represents a group having the same meaning as $R_{41}$. $R_{62}$ represents a group having the same meaning as $R_{41}$, an $R_{41}OCONH$-group, an $R_{41}SO_2NH$-group, an $R_{43}R_{44}NCON(R_{45})$-group, an $R_{43}R_{44}NSO_2N(R_{45})$-group, an $R_{43}O$-group, an $R_{41}S$-group, a halogen atom, or an $R_{41}R_{43}N$-group. $R_{63}$ represents a group having the same meaning as $R_{41}$, an $R_{43}CON(R_{45})$-group, an $R_{43}R_{44}NCO$-group, an $R_{41}SO_2N(R_{44})$-group, an $R_{43}R_{44}NSO_2$-group, an $R_{41}SO_2$-group, an $R_{43}OCO$-group, an $R_{43}O$—$SO_2$-group, a halogen atom, a nitro group, a cyano group, or an $R_{43}CO$-group. e represents an integer from 0 to 4. If a plurality of $R_{62}$'s or $R_{63}$'s are present, they represent either the same group or different groups. Each of $R_{64}$ and $R_{65}$ independently represents an $R_{43}R_{44}NCO$-group, an $R_{41}CO$-group, an $R_{43}R_{44}NSO_2$-group, an $R_{41}OCO$-group, an $R_{41}SO_2$-group, a nitro group, or a cyano group. $Z_1$ represents a nitrogen atom or a =C($R_{66}$)-group (wherein $R_{66}$ represents a hydrogen atom or a group having the same meaning as $R_{63}$). $Z_2$ represents a sulfur atom or an oxygen atom. f represents 0 or 1.

The aliphatic group described above is a saturated or unsaturated, chained or cyclic, straight-chain or branched, or substituted or nonsubstituted aliphatic hydrocarbon group having 1 to 32, and preferably 1 to 22 carbon atoms. Representative examples are methyl, ethyl, propyl, isopropyl, butyl, (t)-butyl, (i)-butyl, (t)-amyl, hexyl, cyclohexyl, 2-ethylhexyl, octyl, 1,1,3,3-tetramethylbutyl, decyl, dodecyl, hexadecyl, and octadecyl.

The above aromatic group is preferably a substituted or nonsubstituted phenyl group, or a substituted or nonsubstituted naphthyl group, which has 6 to 20 carbon atoms.

The above heterocyclic group is a substituted or nonsubstituted heterocyclic group which has 1 to 20, and preferably 1 to 7 carbon atoms, contains a hetero atom selected from a nitrogen atom, an oxygen atom, and a sulfur atom, and is preferably 3- to 8-membered. Representative examples of the heterocyclic group are 2-pyridyl, 2-furyl, 2-imidazolyl, 1-indolyl, 2,4-dioxo-1,3-imidazolidine-5-yl, 2-benzoxazolyl, 1,2,4-triazole-3-yl, and 4-pyrazolyl.

When the aliphatic hydrocarbon group, the aromatic group, and the heterocyclic group described above have their substituents, representative examples of the substituents are a halogen atom, an $R_{47}O$-group, an $R_{46}S$-group, an $R_{47}CON(R_{48})$-group, an $R_{47}R_{48}NCO$- group, an $R_{46}OCON(R_{47})$- group, an $R_{46}SO_2N(R_{47})$-group, an $R_{47}R_{48}NSO_2$-group, an $R_{46}SO_2$-group, an $R_{47}OCO$- group, an $R_{47}R_{48}NCON(R_{49})$ -group, a group having the same meaning as $R_{46}$, an $R_{46}COO$-group, an R47OSO- group, a cyano group, and a nitro group. In this case, $R_{46}$ represents an aliphatic group, an aromatic group, or a heterocyclic group, and each of $R_{47}$, $R_{48}$, and $R_{49}$ independently represents an aliphatic group, an aromatic group, a heterocyclic group, or a hydrogen atom. The meaning of the aliphatic, aromatic, or heterocyclic group is the same as defined above.

Preferable groups as $R_{51}$ to $R_{65}$, and ranges of l, d, e, and f will be described next.

$R_{51}$ is preferably an aliphatic group or an aromatic group. Each of $R_{52}$ and $R_{55}$ is preferably an aromatic group. $R_{53}$ is preferably an aromatic group or a heterocyclic group.

In general formula (Cp-3), $R_{54}$ is preferably an $R_{41}CONH$-group or an $R_{41}R_{43}N$-group. Each of $R_{56}$ and $R_{57}$ is preferably an aliphatic group, an aromatic group, an $R_{41}O$-group, or an $R_{41}S$-group. $R_{58}$ is preferably an aliphatic group or an aromatic group. In general formula (Cp-6), $R_{59}$ is preferably a chlorine atom, an aliphatic group, or an $R_{41}CONH$-group. d is preferably 1 or 2. $R_{60}$ is preferably an aromatic group. In general formula (Cp-7), $R_{59}$ is preferably an $R_{41}CONH$-group.

In general formula (Cp-7), d is preferably 1 $R_{61}$ is preferably an aliphatic group or an aromatic group. In general formula (Cp-8), e is preferably 0 or 1. $R_{62}$ is preferably an $R_{41}OCONH$- group, an $R_{41}CONH$-group, or an $R_{41}SO_2NH$-group, and the substitution position of these groups is preferably the 5-position of a naphthol ring. In general formula (Cp-9), $R_{63}$ is preferably an $R_{41}CONH$- group, an $R_{41}SO_2NH$-group, an $R_{41}R_{43}NSO_2$-group, an $R_{41}SO_2$-group, an $R_{41}R_{43}NCO$-group, a nitro group, or a cyano group, and e is preferably 1 or 2. In general formula (Cp-10), $R_{63}$ is preferably an $(R_{43})2NCO$-group, an $R_{43}OCO$-group, or an $R_{43}CO$-group, and l, is preferably 1 or 2.

In general formula (Cp-11), $R_{54}$ is preferably an aliphatic group, an aromatic group, or an $R_{41}CONH$-group, and f is preferably 1.

In a compound represented by general formula (I), each of groups represented by $R_1$ and $R_2$ independently represents a hydrogen atom or a substituent. Examples of the substituent are an aryl group (e.g., phenyl, naphthyl, p-methoxyphenyl, p-hydroxyphenyl, p-nitrophenyl, or o-chlorophenyl), an alkyl group (e.g., methyl, ethyl, isopropyl, propyl, tert-butyl, tert-amyl, isobutyl, sec-butyl, octyl, methoxymethyl, 1-methoxyethyl, or 2-chloroethyl), a halogen atom (fluoro, chloro, bromo, or iodo), an alkoxyl group (e.g., methoxy, ethoxy, isopropoxy, propoxy, tert-butoxy, isobutoxy, butoxy, octyloxy, 2-methoxyethoxy, 2-chloroethoxy, nitromethoxy, 2-cyanoethoxy, 2-carbamoylethoxy, or 2-dimethylcarbamoylethoxy), an aryloxy group (e.g., phenoxy, naphthoxy, or p-methoxyphenoxy), an alkylthio group (e.g., methylthio, ethylthio, isopropylthio, propylthio, tert-butylthio, isobutylthio, sec-butylthio, octylthio, or 2-methoxyethylthio), an arylthio group (e.g., phenylthio, naphthylthio, or p-methoxyphenylthio), an amino group (e.g., amino, methylamino, phenylamino, dimethylamino, diethylamino, diisopropylamino, or phenylmethylamino), a carbamoyl group (e.g., carbamoyl, methylcarbamoyl, dimethylcarbamoyl, diethylcarbamoyl, diisopropylcarbamoyl, ethylcarbamoyl, isopropylcarbamoyl, tert-butylcarbamoyl, or phenylcarbamoyl), a sulfamoyl group (e.g., sulfamoyl, methylsulfamoyl, ethylsulfamoyl, isopropylsulfamoyl, phenylsulfamoyl, octylsulfamoyl, dimethylsulfamoyl, diethylsulfamoyl, diisopropylsulfamoyl, dihexylsulfamoyl, or phenylsulfamoyl), alkoxycarbonyl (e.g., methoxycarbonyl, propoxycarbonyl, isopropoxycarbonyl, tert-butoxycarbonyl, tert-amyloxycarbonyl, or octyloxycarbonyl), aryloxycarbonyl (e.g., phenoxycarbonyl or p-methoxyphenoxycarbonyl), an acylamino group (e.g., acetylamino, propanoylamino, pentanoylamino, N-methylacetylamino, or benzoylamino), a sulfonamide group (e.g., methanesulfonamide, ethanesulfonamide, pentanesulfonamide, benzenesulfonamide, or p-toluenesulfonamide), an alkoxycarbonylamino group (e.g., methoxycarbonylamino, isopropoxycarbonylamino, tert-butoxycarbonylamino, or hexyloxycarbonylamino), an aryloxycarbonylamino group (e.g., phenoxycarbonylamino), an ureido group (e.g., 3-methylureido or 3-phenylureido), a cyano group, or a nitro group.

Although $R_1$, and $R_2$ may be the same or different, the sum of the chemical formula weights of the two groups is preferably less than 120. A substituent is preferably an alkyl group, a halogen atom, or an alkoxyl group, and most preferably an alkyl group. In particular, it is preferable that both of $R^1$ and $R^2$ are methyl.

In general formula (I), each of groups represented by $R_3$ and $R_4$ independently represents a hydrogen atom or an alkyl group. Examples of the alkyl group are methyl, ethyl, isopropyl, tert-butyl, isobutyl, hexyl, and 2-methoxyethyl. Each of $R_3$ and $R_4$ is preferably a hydrogen atom, a methyl group, or an ethyl group, and most preferably a hydrogen atom.

In general formula (I), a group represented by $R_5$ represents a nonsubstituted phenyl group, a non-substituted primary alkyl group, or a primary alkyl group substituted with a group other than an aryl group. Examples of the alkyl group are ethyl, propyl, butyl, isobutyl, pentyl, isopentyl, 2-methylbutyl, hexyl, 2-methylpentyl, 3-methylpentyl, 4-methylpentyl, 2-ethylbutyl, heptyl, or octyl. Examples of the substituent are a halogen atom, an alkoxyl group, an alkylthio group, an amino group, a carbamoyl group, a sulfamoyl group, an alkoxycarbonyl group, an acylamino group, a sulfonamide group, an alkoxycarbonylamino group, an ureido group, a cyano group, a nitro group, and a group represented by $-CO_2CH_2CO_2R_{70}$. Examples of the respective groups are those enumerated above as the substituents of $R_1$ and $R_2$ except for the groups containing an aryl group. $R_{70}$ represents a nonsubstituted alkyl group (e.g., propyl, butyl, isobutyl, pentyl, isopentyl, or hexyl) having 3 to 6 carbon atoms. $R_5$ may be substituted with two or more types of substituents.

Preferable examples of the substituent are fluoro, chloro, an alkoxyl group, a carbamoyl group, an alkoxycarbonyl group, a cyano group, a nitro group, or $-CO_2CH_2CO_2R_{70}$. Of these examples, a most preferable example is an alkoxycarbonyl group or $-CO_2CH_2CO_2R_{70}$.

Preferable examples of $R_5$ are a phenyl group, a nonsubstituted primary alkyl group, and a primary alkyl group substituted with the groups exemplified above as the preferable examples of $R_5$. $R_5$ is most preferably a nonsubstituted primary alkyl group having 3 to 5 carbon atoms or a primary alkyl group substituted with an alkoxycarbonyl group.

A group represented by INH in general formula (I) represents a group having a development inhibiting function and is preferably a group represented by any one of the following general formulas (INH-1) to (INH-13)

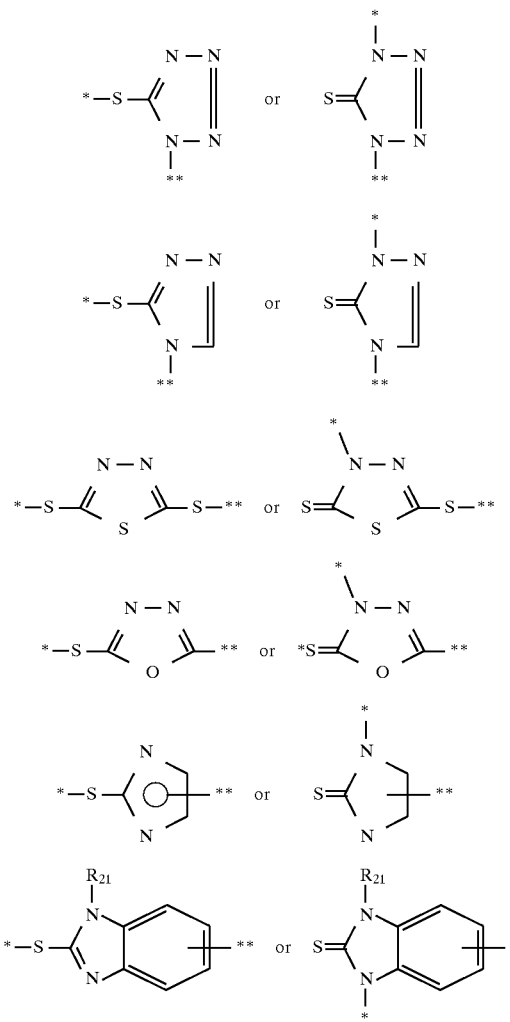

wherein $R_{21}$ represents a hydrogen atom or a substituted or unsubstituted hydrocarbon group (e.g., methyl, ethyl, propyl, and phenyl).

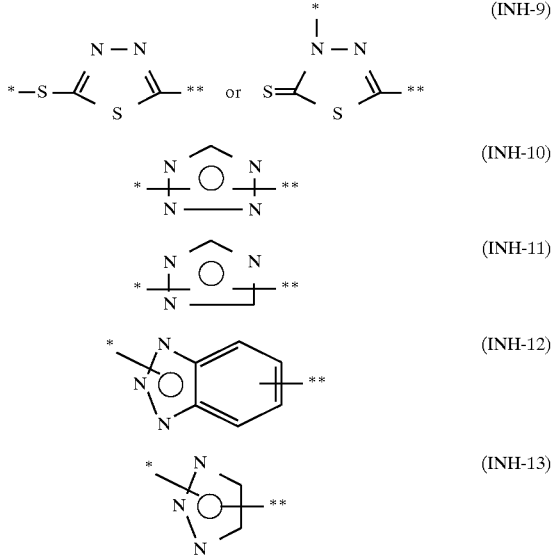

(wherein symbol * represents a position where the group is bonded with a group represented by —$CR_3(R_4)$— in the compound represented by general formula (I), and symbol ** represents a position where the group is bonded with R5.)

Of these groups, INH is preferably (INH-1), (INH-2), (INH-3), (INH-4), (INH-9), and (INH-12), and most preferably (INH-1).

The compound represented by general formula (I) of the present invention can be used in any layer of the photosensitive material. However, the compound is preferably added to photosensitive silver halide emulsion layers and/or their neighboring layers, more preferably photosensitive silver halide emulsion layers, and most preferably red-sensitive silver halide emulsion layers. The total addition amount of the compound to the photosensitive material is normally $3 \times 10^{-7}$ to $1 \times 10^{-3}$ mol/m$^2$, preferably $3 \times 10^{-6}$ to $5 \times 10^{-4}$ mol/m$^2$, and more preferably $1 \times 10^{-5}$ to $2 \times 10^{-4}$ mol/m$^2$.

The compound represented by general formula (I) of the present invention can be added to the photosensitive material in the same manner as common couplers as will be described later.

Practical examples of the compound represented by general formula (I) of the present invention will be presented below, but not limited to these examples.

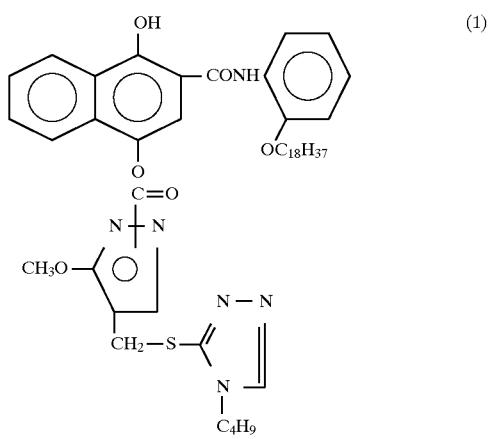

(1)

A part of structural formula,
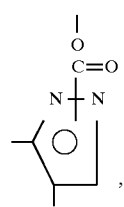
represents that an —OC(=O)-group combines with one of two nitrogen atoms froming a pyrazole ring. The representation is used identically for the following compounds.
(2)
(3)

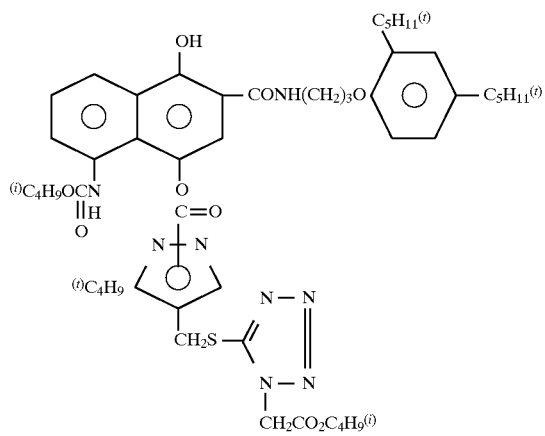
(4)
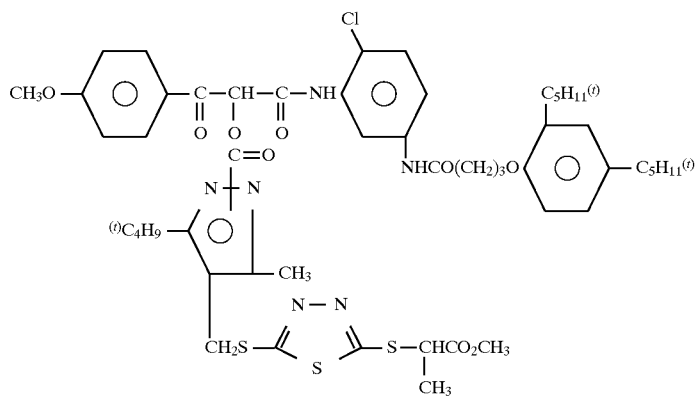
(5)
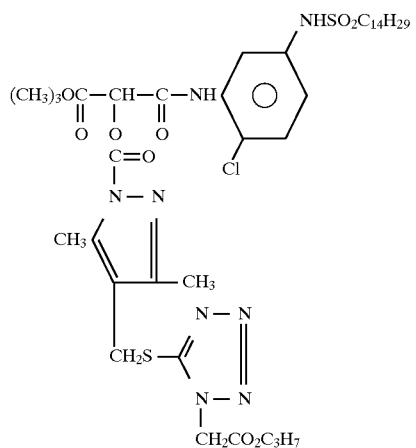
(6)

(7)
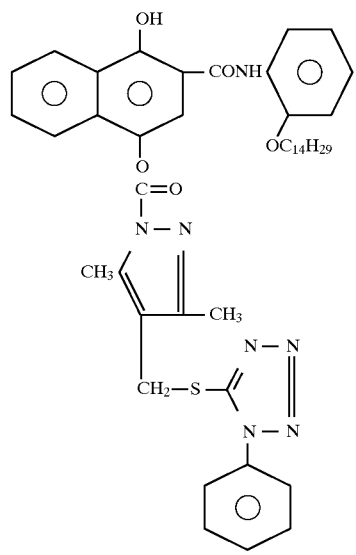
(8)
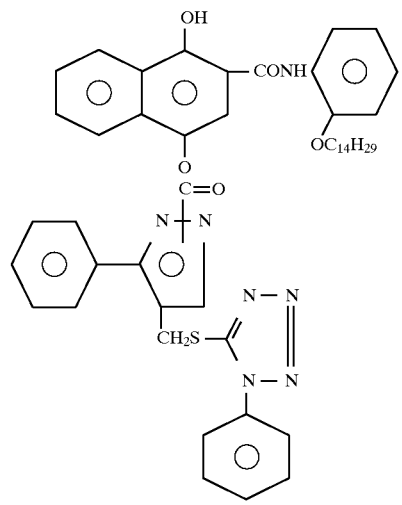
(9)
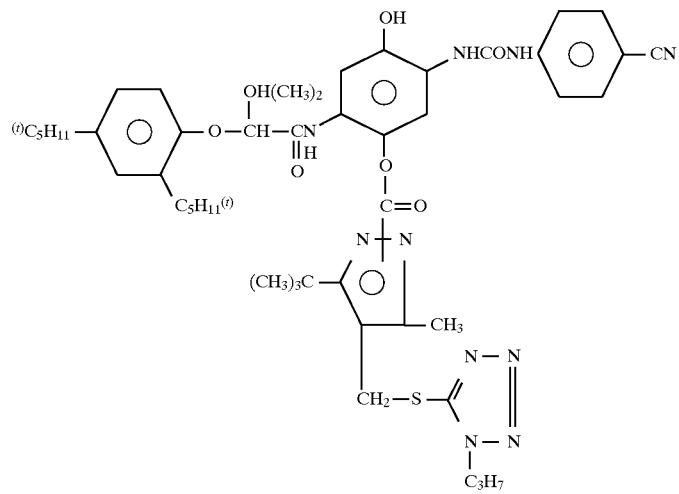

-continued
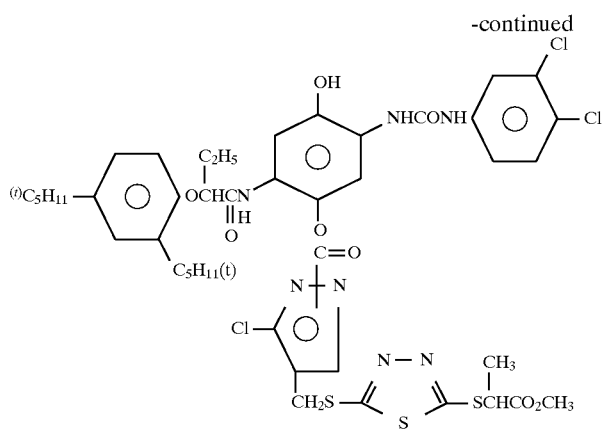
(10)
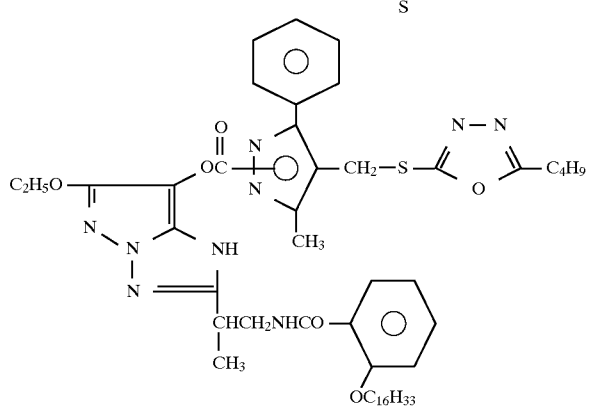
(11)
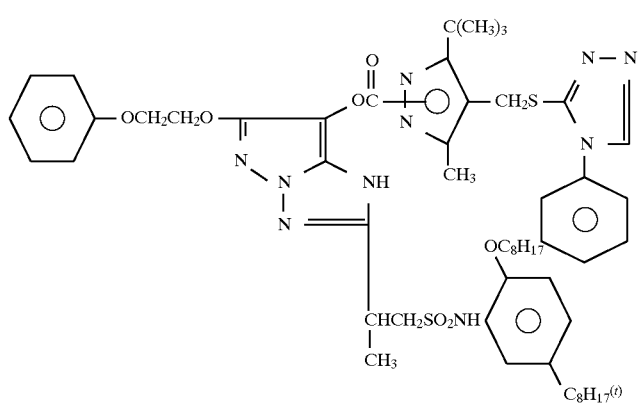
(12)
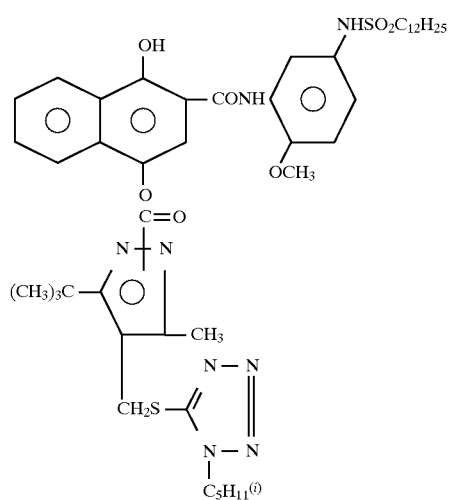
(13)

-continued
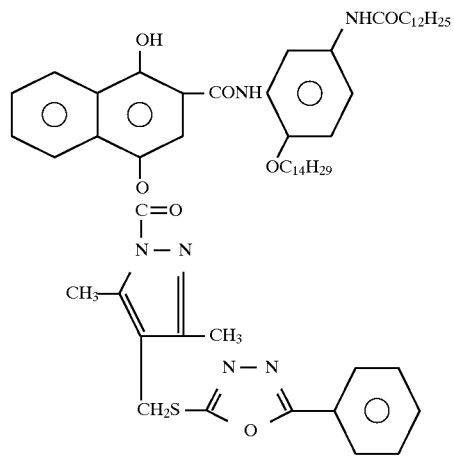 (14)
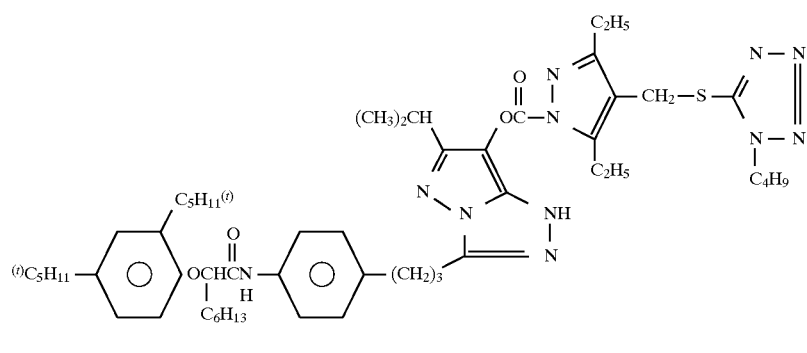 (15)
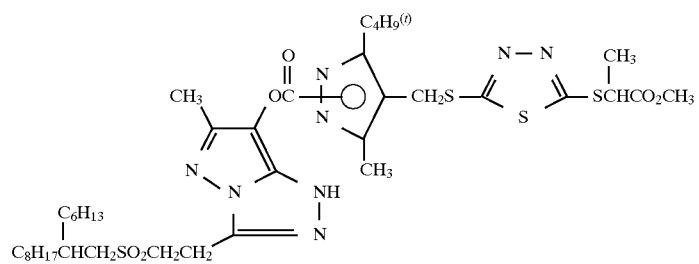 (16)
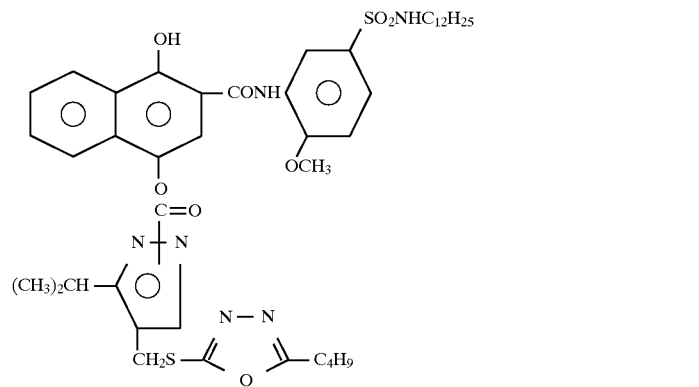 (17)

(18)
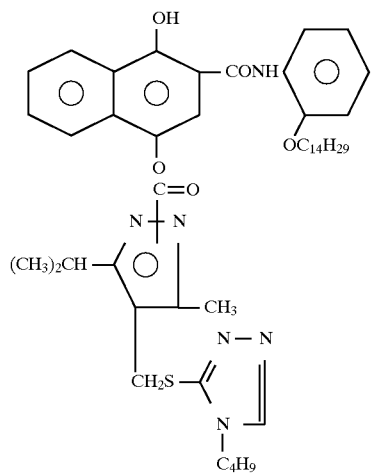
(19)
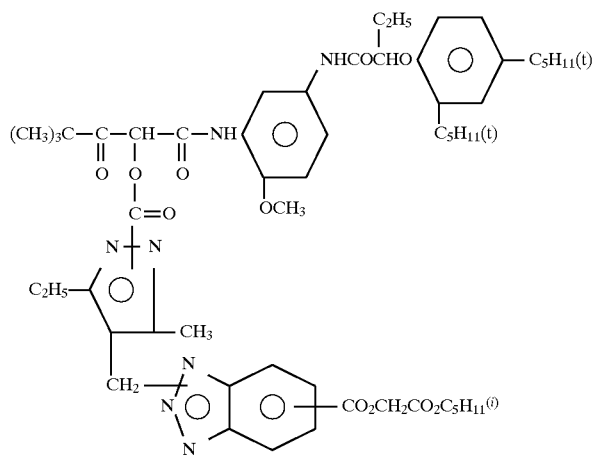
(20)
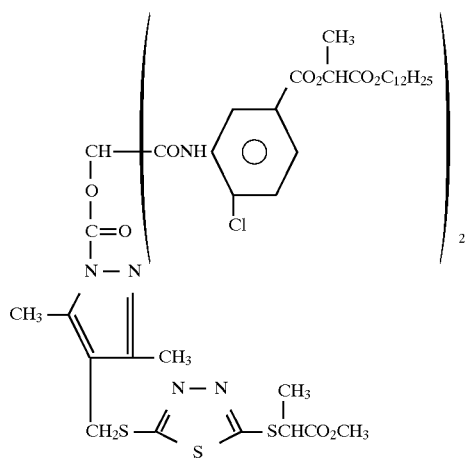

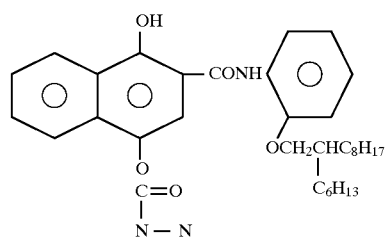
(21)
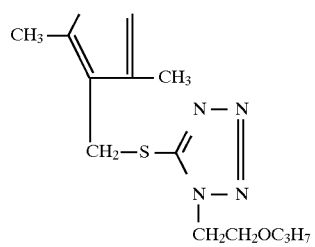
(22)
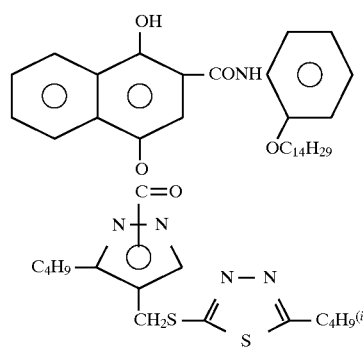
(23)
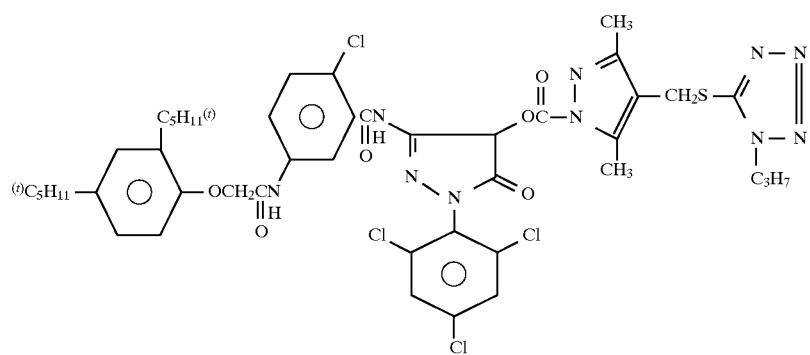
(24)
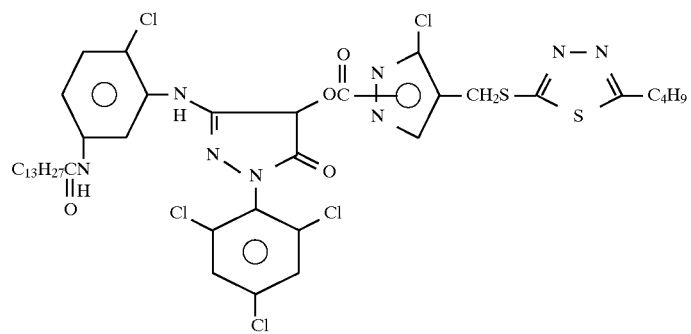

(25)
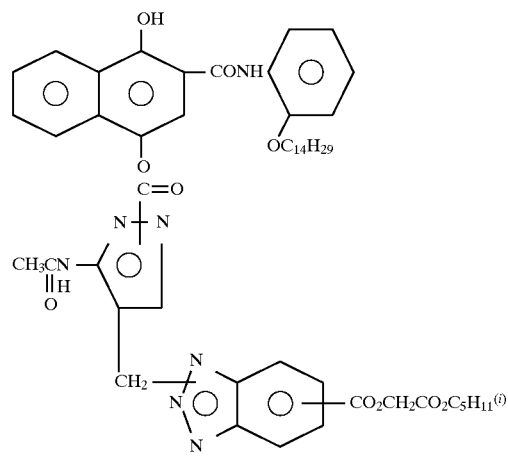
(26)
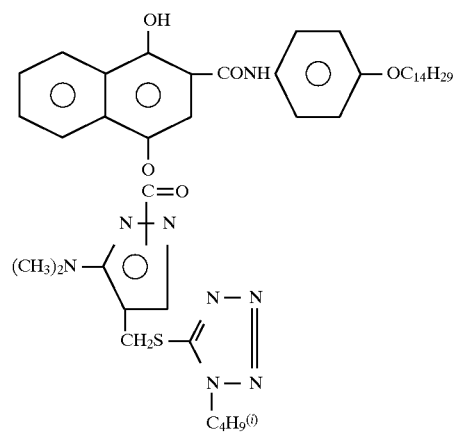
(27)
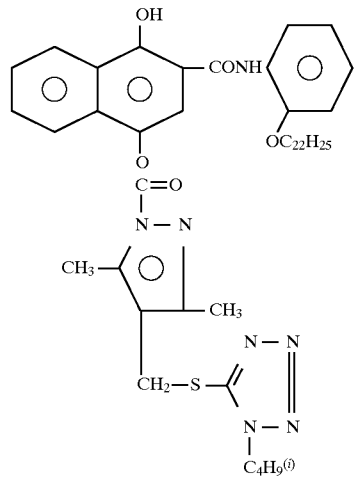

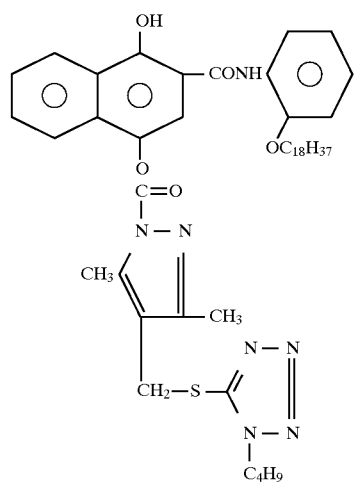
(28)
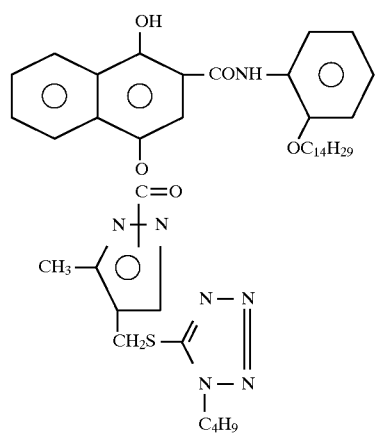
(29)
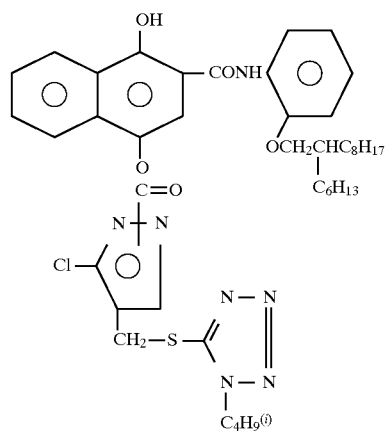
(30)

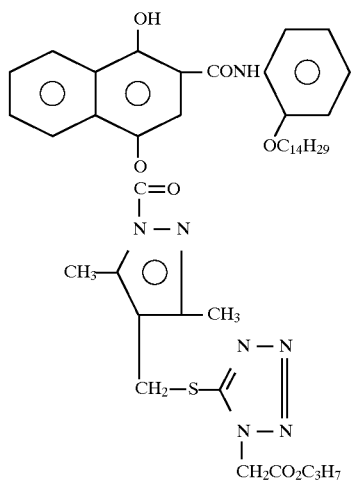
(31)
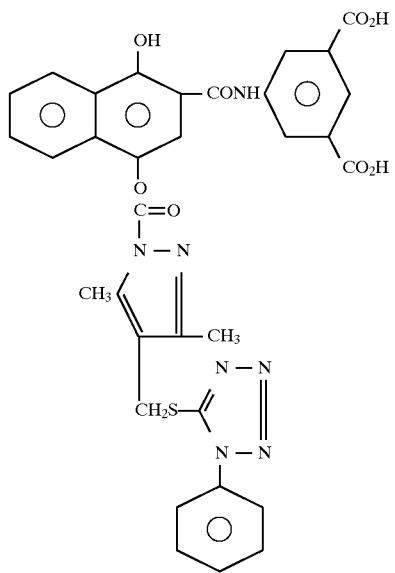
(32)
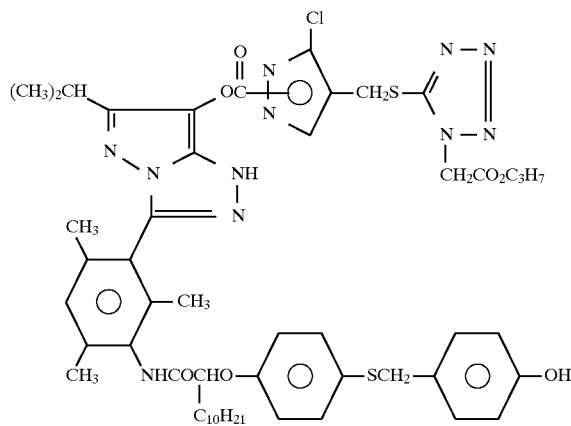
(33)

-continued
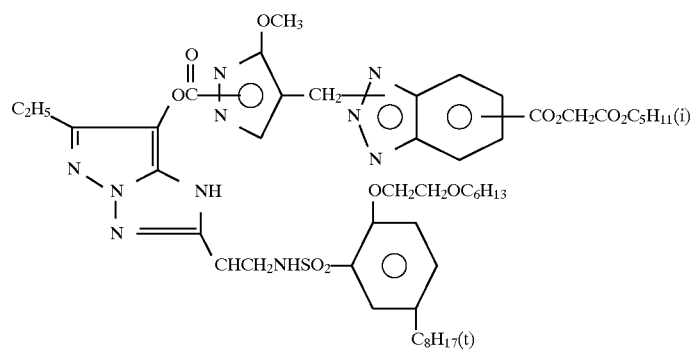
(34)
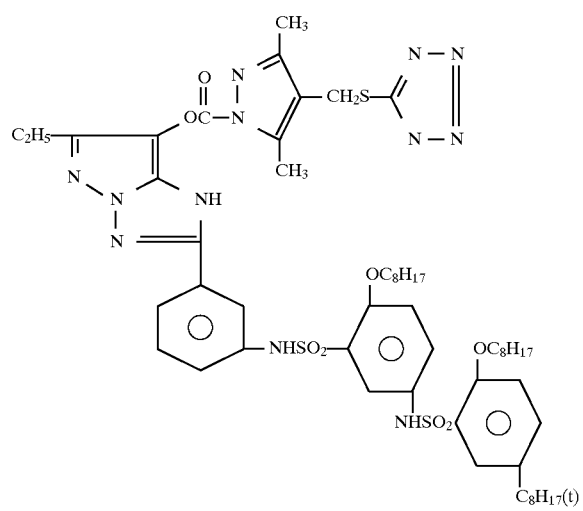
(35)
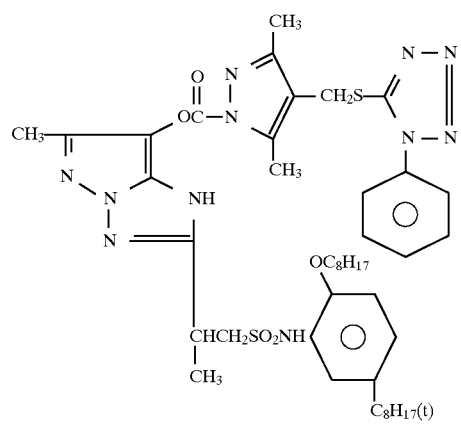
(36)

-continued
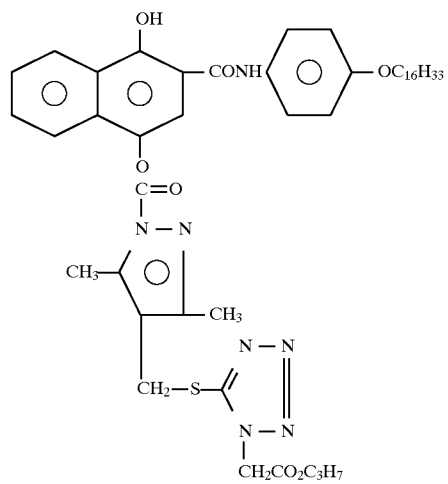
(37)
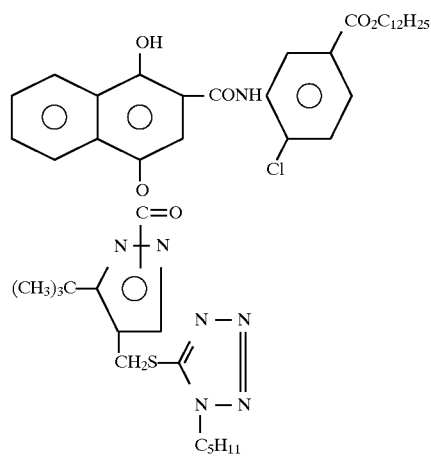
(38)
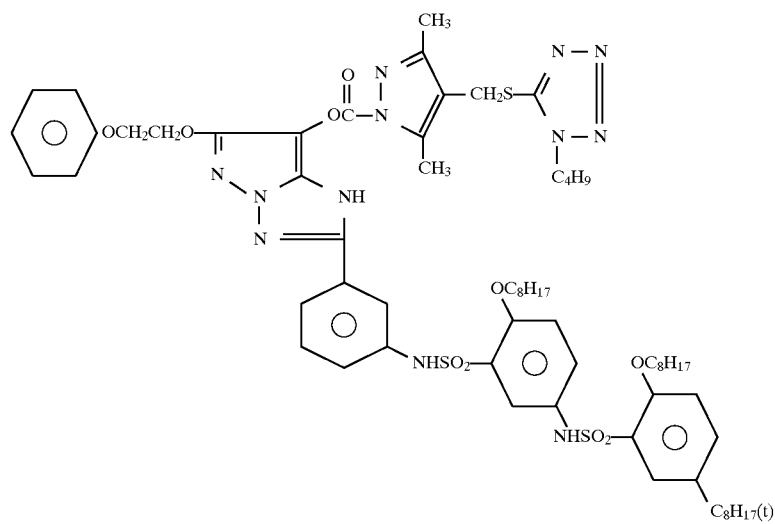
(39)

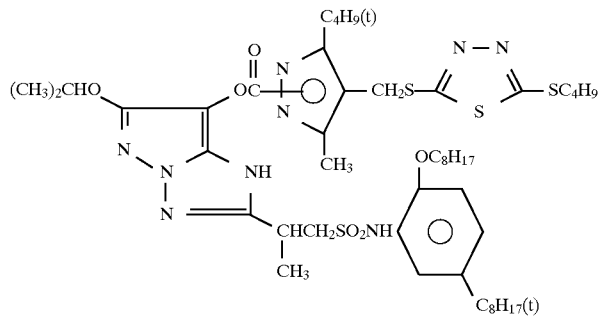
(40)
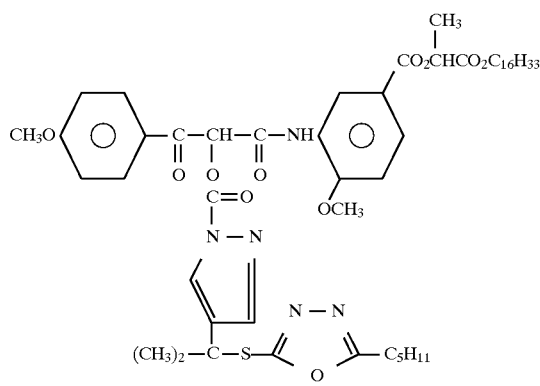
(41)
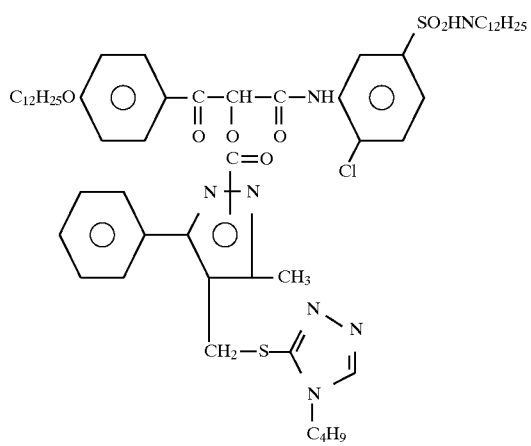
(42)
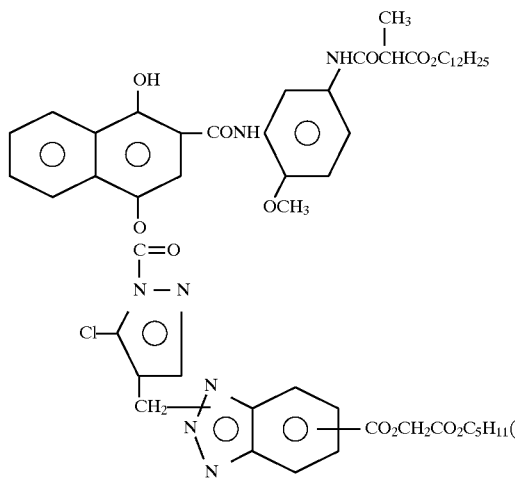
(43)

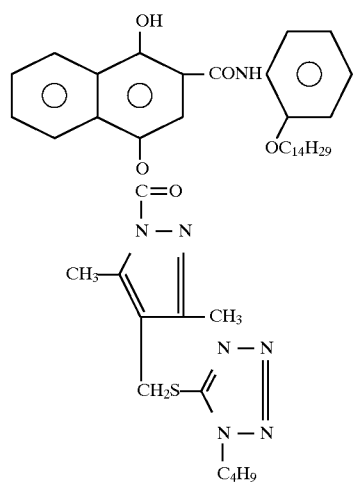
(44)
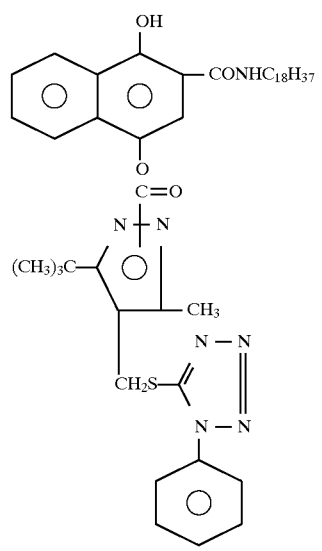
(45)
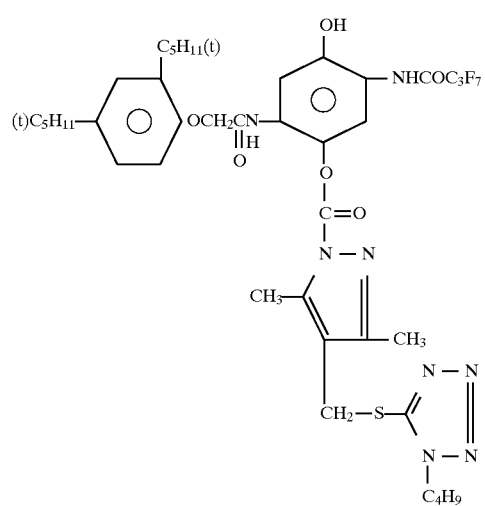
(46)

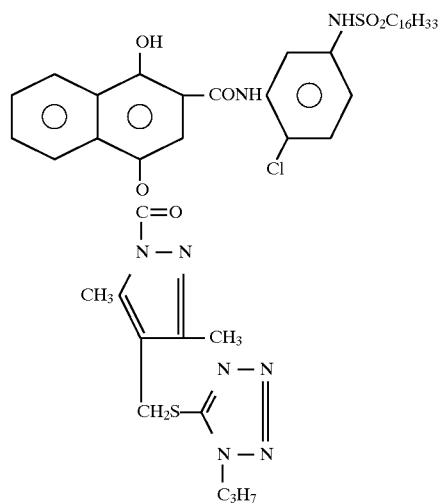
(47)
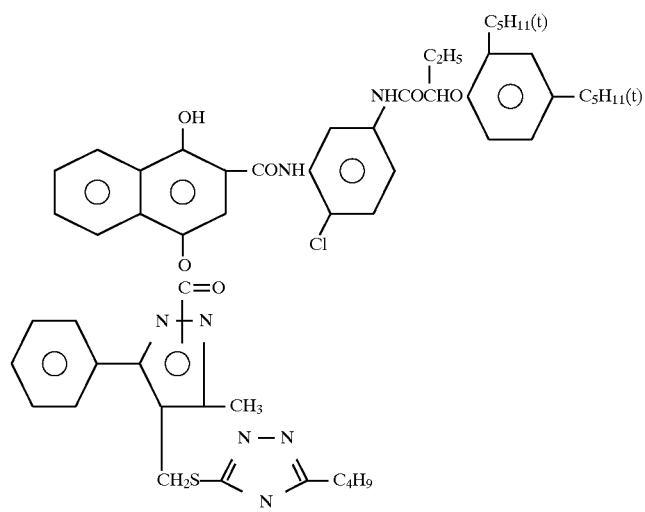
(48)
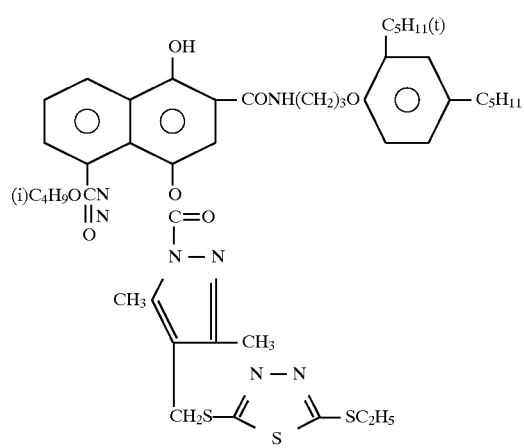
(49)

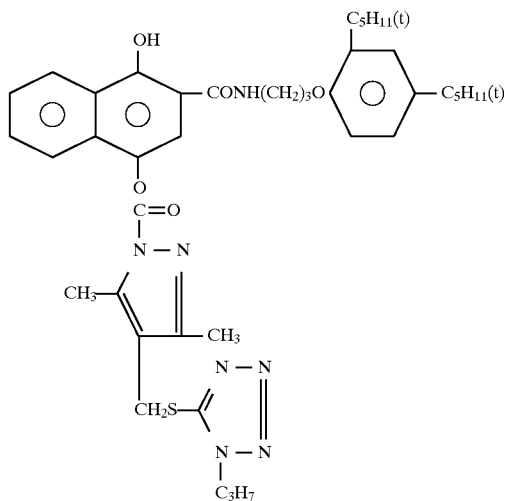
(50)
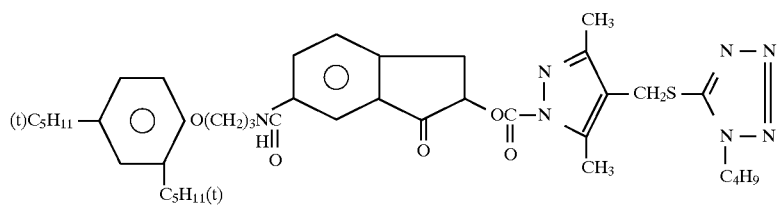
(51)
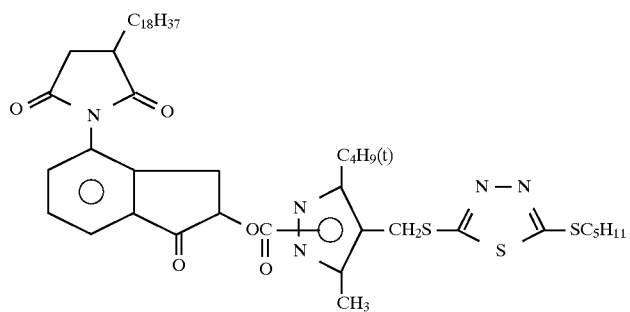
(52)
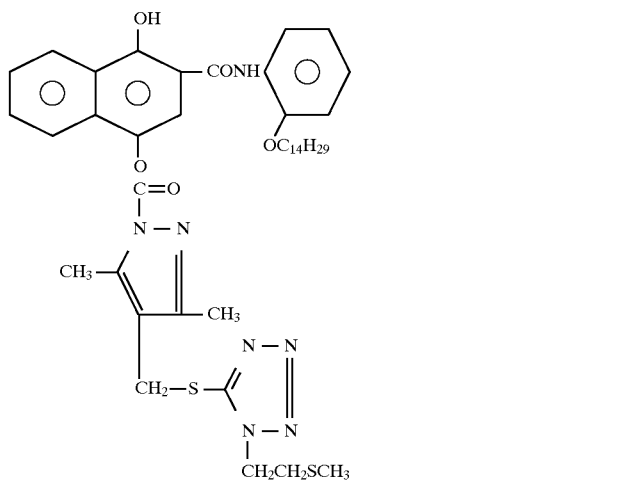
(53)

-continued
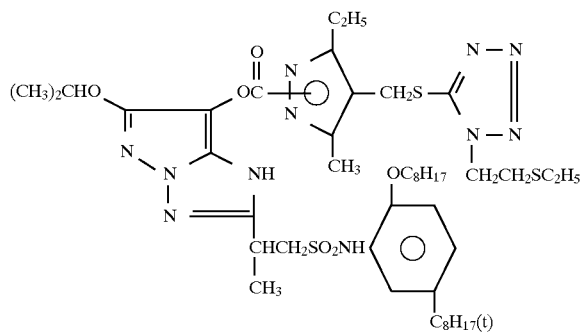
(54)
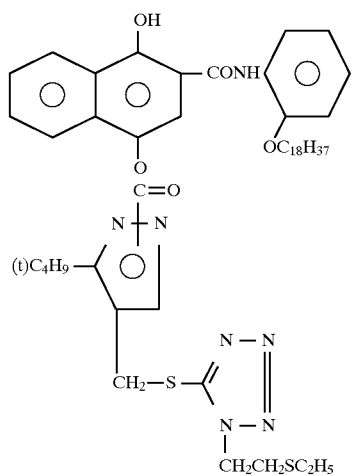
(55)
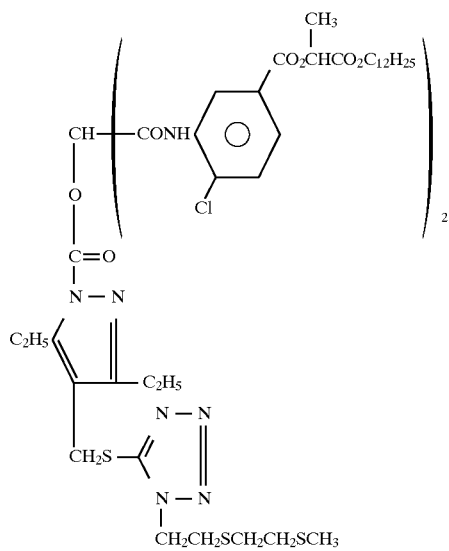
(56)

(57)
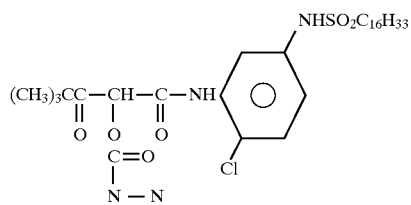
(58)
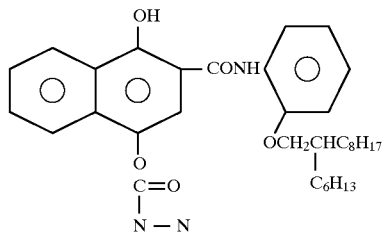
(59)
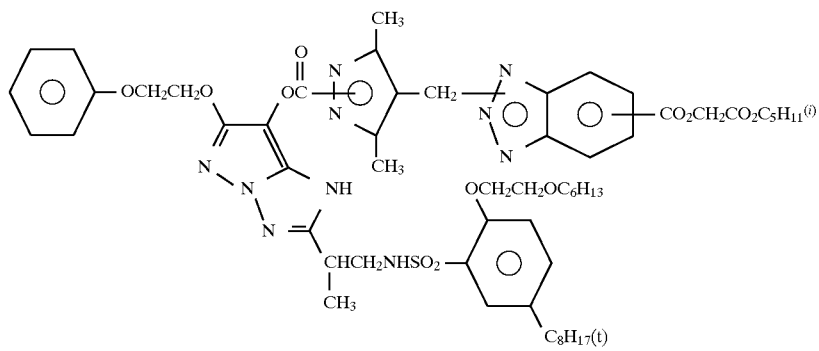

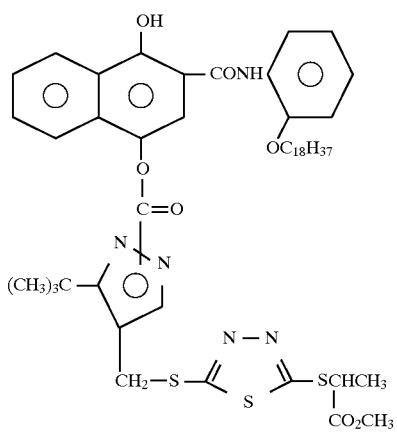

(60)

The compounds of the present invention can be synthesized by using 4-hydroxymethylpyrazole or its equivalent as a raw material in accordance with the route indicated in scheme (1).

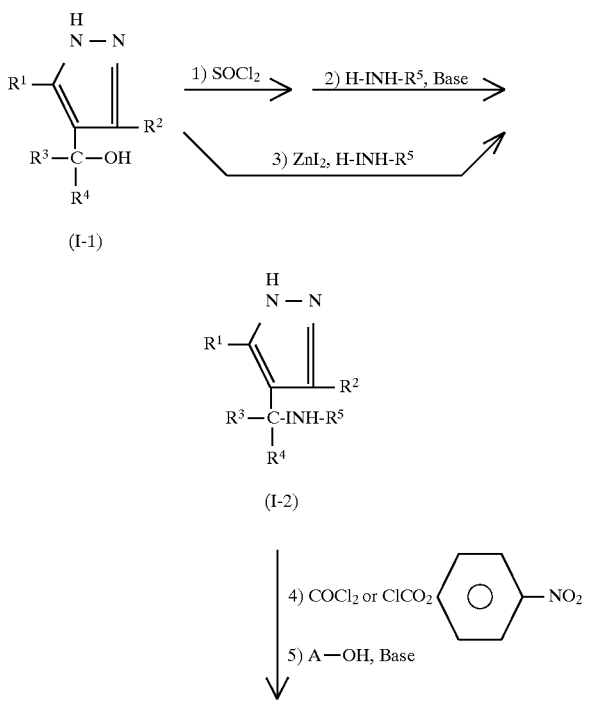

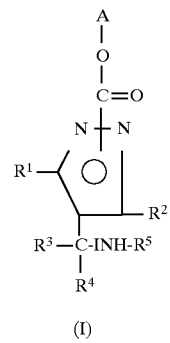

($R^1$ to $R^5$, INH, and A have the same meanings as in general formula I)

That is, (I-1) is converted into a chloride or its equivalent by a reaction with thionyl chloride or its analogous compound, and the resultant product is reacted with H—INH—$R^5$ in the presence of a base, thereby obtaining (I-2). (I-2) can also be obtained by reacting (I-1) with H—INH—$R^5$ in the presence of a Lewis acid such as zinc iodide.

(I-2) obtained in this manner is reacted with phosgene or its equivalent in either the presence or absence of a base and further reacted with A—OH in the presence of a base. As a result, (I) of interest can be obtained.

Practical synthesis examples of the compound of the present invention will be described below, but not limited to these examples.

(Synthesis Example 1) Synthesis of compound (8)

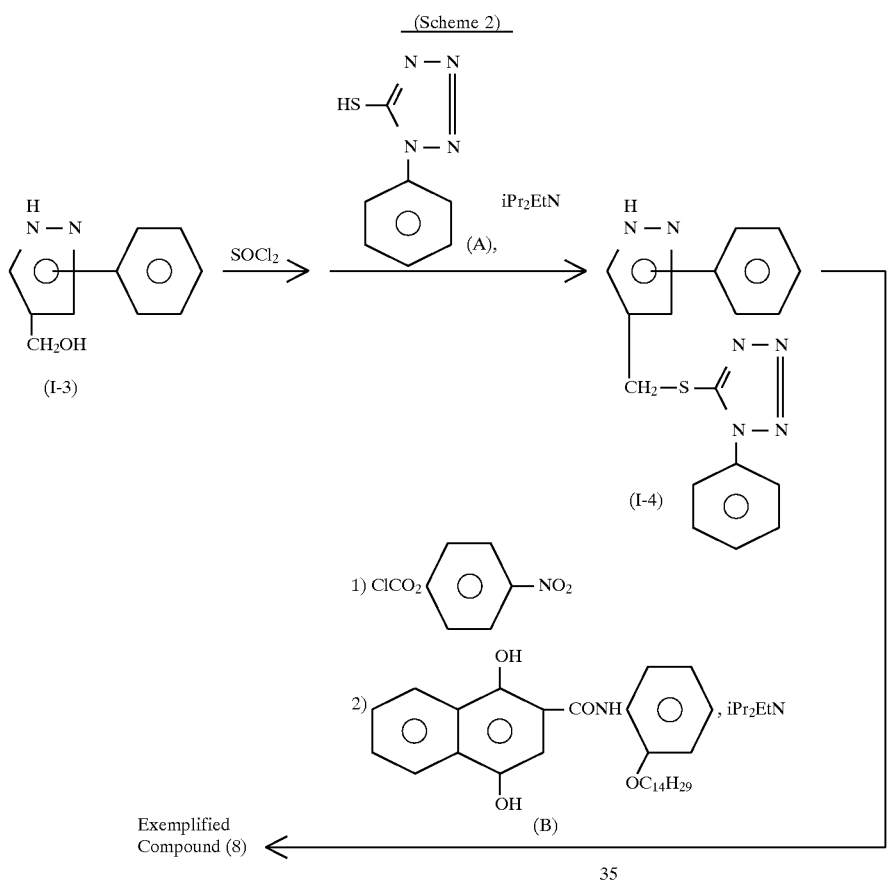

(I-3) (10 mmol) is suspended in chloroform (30 ml), and thionyl chloride (20 mmol) is added to the resultant suspension to cause a reaction at 50° C. for one hour. Thereafter, the solvent is distilled off. The obtained residue is added to a dimethylformamide (30 ml) solution of A (10 mmol) and diisopropylethylamine (20 mmol) to cause a reaction for one hour, and the resultant solution is poured in ice water (200 ml). After chloroform is added and the resultant solution is stirred, the water phase is separated, and the obtained organic layer is washed with water (100 ml) twice. The resultant solution is dried by sodium sulfate and condensed to obtain (I-4).

The obtained (I-4) is dissolved in chloroform (30 ml), and nitrophenyl chlorocarbonate (10 mmol) is added to the resultant solution to cause a reaction for one hour. Thereafter, an ethyl acetate (50 ml) solution of B (10 mmol) is added, and diisopropylethylamine (50 mmol) is added to cause a reaction for one hour. 1N hydrochloric acid is added to stop the reaction, and the resultant solution is diluted with ethyl acetate (100 ml). The organic layer is washed with water, dried by sodium sulfate, and condensed. The obtained residue is purified through a silica gel column chromatography (used elute is ethyl acetate:hexane =1:3) to obtain 1.94 g (yield 23%) of exemplified compound (8). The melting point is 101.5° C. to 102.5° C.

(Synthesis Example 2) synthesis of compound (28)

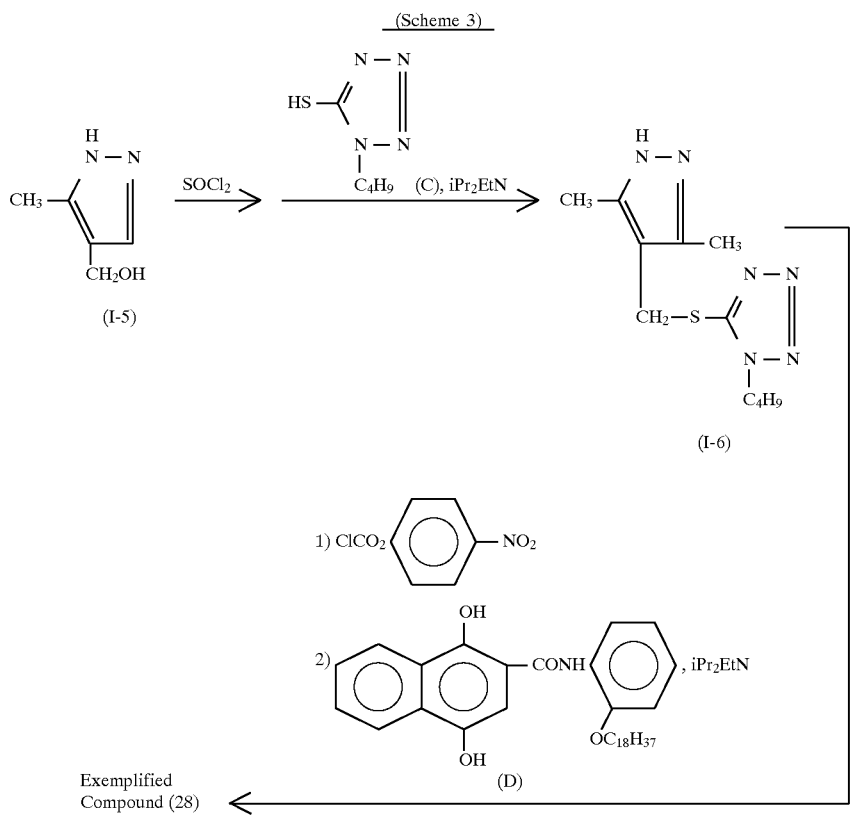

The exemplified compound (28) can be synthesized by using (I-5) as a raw material following the same procedures as for exemplified compound (8) as indicated in scheme 3. The yield is 31%, and the melting point is 68.0° C. to 69.0° C.

In the photosensitive material of the present invention, at least one of blue-, green-, and red-sensitive silver halide emulsion layers need only be formed on a support, and the number and order of the silver halide emulsion layers and non-photosensitive layers are not particularly limited. A typical example is a silver halide photographic photosensitive material having, on its support, at least one photosensitive layer constituted by a plurality of silver halide emulsion layers which are sensitive to essentially the same color but have different sensitivities. This photosensitive layer is a unit sensitive layer which is sensitive to one of blue light, green light, and red light. In a multilayered silver halide color photographic photosensitive material, such unit photosensitive layers are generally arranged in an order of red-, green-, and blue-sensitive layers from a support. However, in accordance with the application, this arrangement order may be reversed, or photosensitive layers sensitive to the same color may sandwich another photosensitive layer sensitive to a different color.

Non-photosensitive layers such as various types of interlayers may be formed between the silver halide photosensitive layers and as the uppermost layer and the lowermost layer.

The interlayer may contain, e.g., couplers and DIR compounds as described in JP-A-61-43748, JP-A-59-113438, JP-A-59-113440, JP-A-61-20037, and JP-A-61-20038 or a color mixing inhibitor which is normally used.

As a plurality of silver halide emulsion layers constituting each unit photosensitive layer, a two-layered structure of high- and low-sensitivity emulsion layers can be preferably used as described in West German Patent 1,121,470 or British Patent 923,045. In this case, layers are preferably arranged such that the sensitivity is sequentially decreased toward a support, and a non-photosensitive layer may be formed between the respective silver halide emulsion layers. In addition, as described in JP-A-57-112751, JP-A-62-200350, JP-A-62-206541, and JP-A-62-206543, layers may be arranged such that a low-sensitivity emulsion layer is formed remotely from a support and a high-sensitivity layer is formed close to the support.

More specifically, layers may be arranged from the farthest side from a support in an order of low-sensitivity blue-sensitive layer (BL)/high-sensitivity blue-sensitive layer (BH)/high-sensitivity green-sensitive layer (GH)/low-sensitivity green-sensitive layer (GL)/high-sensitivity red-sensitive layer (RH)/low-sensitivity red-sensitive layer (RL), an order of BH/BL/GL/GH/RH/RL, or an order of BH/BL/GH/GL/RL/RH.

In addition, as described in JP-B-55-34932 ("JP-B" means Published Examined Japanese Patent Application), layers may be arranged from the farthest side from a support in an order of blue-sensitive layer/GH/RH/GL/RL. Furthermore, as described in JP-A-56-25738 and JP-A-62-63936, layers may be arranged from the farthest side from a support in an order of blue-sensitive layer/GL/RL/GH/RH.

As described in JP-B-49-15495, three layers may be arranged such that a silver halide emulsion layer having the highest sensitivity is arranged as an upper layer, a silver halide emulsion layer having sensitivity lower than that of the upper layer is arranged as an inter-layer, and a silver halide emulsion layer having sensitivity lower than that of the interlayer is arranged as a lower layer, i.e., three layers having different sensitivities may be arranged such that the sensitivity is sequentially decreased toward the support. When a layer structure is constituted by three layers having different sensitivities, these layers may be arranged in an order of medium-sensitivity emulsion layer/high-sensitivity emulsion layer/low-sensitivity emulsion layer from the farthest side from a support in a layer sensitive to one color as described in JP-A-59-202464.

In addition, an order of high-sensitivity emulsion layer/low-sensitivity emulsion layer/medium-sensitivity emulsion layer or low-sensitivity emulsion layer/medium-sensitivity emulsion layer/high-sensitivity emulsion layer may be adopted. Furthermore, the arrangement can be changed as described above even when four or more layers are formed.

In order to improve color reproducibility, a donor layer (CL) with an interlayer effect, which is described in U.S. Pat. No. 4,663,271, 4,705,744, or 4,707,436, JP-A-62-160448, or JP-A-63-89580 and different from the main photosensitive layers BL, GL, and RL in spectral sensitivity distribution, is preferably formed adjacent to or close to the main photosensitive layers.

As described above, various layer types and arrangements can be selected in accordance with the application of the photosensitive material.

A preferable silver halide contained in photographic emulsion layers of the photographic photosensitive material of the present invention is silver iodobromide, silver iodochloride, or silver iodochlorobromide containing about 30 mol% or less of silver iodide. The most preferable silver halide is silver iodobromide or silver iodochlorobromide containing about 2 mol% to about 25 mol% of silver iodide.

Silver halide grains contained in the photographic emulsion may have regular crystals such as cubic, octahedral, or tetradecahedral crystals, irregular crystals such as spherical or tabular crystals, crystals having crystal defects such as twined crystal faces, or composite shapes thereof.

The silver halide may consist of fine grains having a grain size of about 0.2 $\mu$m or less or large grains having a projected area diameter of about 10 $\mu$m, and an emulsion may be either a polydisperse or monodisperse emulsion.

The silver halide photographic emulsion which can be used in the photosensitive material of the present invention can be prepared by methods described in, for example, "I. Emulsion preparation and types," Research Disclosure (RD) No. 17,643 (December, 1978), pp. 22 to 23, RD No. 18,716 (November, 1979), page 648 and RD No. 307,105 (November 1989), pp. 863 to 865; P. Glafkides, "Chemie et Phisique Photographique", Paul Montel, 1967; G. F. Duffin, "Photographic Emulsion Chemistry", Focal Press, 1966; and V. L. Zelikman et al., "Making and Coating Photographic Emulsion", Focal Press, 1964.

Monodisperse emulsions described in, for example, U.S. Pat. Nos. 3,574,628 and 3,655,394 and British Patent 1,413,748 are also preferred.

Also, tabular grains having an aspect ratio of about 5 or more can be used in the present invention. The tabular grains can be easily prepared by methods described in, e.g., Gutoff, "Photographic Science and Engineering", Vol. 14, PP. 248 to 257 (1970); U.S. Pat. Nos. 4,434,226, 4,414,310, 4,433,048, and 4,439,520, and British Patent 2,112,157.

The crystal structure may be uniform, may have different halogen compositions in the interior and the surface layer thereof, or may be a layered structure. Alternatively, the crystal may be formed of silver halides having a different composition which are opitaxially bonded or a silver halide and a compound other than a silver halide such as silver rhodanide or zinc oxide which are bonded each other. A mixture of grains having various types of crystal shapes may be used.

The above emulsion may be any of a surface latent image type emulsion which mainly forms a latent image on the surface of a grain, an internal latent image type emulsion which forms a latent image in the interior of a grain, and an emulsion of another type which has latent images on the surface and in the interior of a grain. However, the emulsion must be a negative type emulsion. In this case, the internal latent image type emulsion may be a core/shell internal latent image type emulsion described in JP-A-63-264740. A method of preparing this core/shell internal latent image type emulsion is described in JP-A-59-133542. Although the thickness of a shell of this emulsion depends on, e.g., development procedures, it is preferably 3 to 40 nm, and most preferably 5 to 20 nm.

The silver halide emulsion layer is normally subjected to physical ripening, chemical ripening, and spectral sensitization steps before it is used. Additives for use in these steps are described in Research Disclosure Nos. 17,643, 18,716, and 307,105, and they are summarized in the following table.

In the photosensitive material of the present invention, it is possible to simultaneously use, in a single layer, two or more types of emulsions different in at least one of characteristics of the photosensitive silver halide emulsion, i.e., a grain size, a grain size distribution, a halogen composition, a grain shape, and a sensitivity.

It is also possible to preferably use surface-fogged silver halide grains described in U.S. Pat. No. 4,082,553, internally fogged silver halide grains described in U.S. Pat. No. 4,626,498 and JP-A-59-214852, and colloidal silver, in photosensitive silver halide emulsion layers and/or essentially non-photosensitive hydrophilic colloid layers. The internally fogged or surface-fogged silver halide grain means a silver halide grain which can be developed uniformly (non-imagewise) regardless of whether the location is a non-exposed portion or an exposed portion of the photosensitive material. A method of preparing the internally fogged or surface-fogged silver halide grain is described in U.S. Pat. No. 4,626,498 and JP-A-59-214852.

The silver halide which forms the cores of internally fogged core/shell type silver halide grains may have either a single halogen composition or different halogen compositions. As the internally fogged or surface-fogged silver halide, any of silver chloride, silver chlorobromide, silver bromoiodide, and silver bromochloroiodide can be used. Although the grain size of these fogged silver halide grains is not particularly limited, the average grain size is preferably 0.01 to 0.75 $\mu$m, and most preferably 0.05 to 0.6 $\mu$m. Since the grain shape is not particularly limited either, regular grains may be used. The emulsion may be a polydisperse emulsion but is preferably a monodisperse emulsion (in which at least 95% in weight or the number of grains of silver halide grains have grain sizes falling within a range of ±40% of an average grain size).

In the present invention, it is preferable to use a non-photosensitive fine grain silver halide. The non-photosensitive fine grain silver halide preferably consists of silver halide grains which are not exposed during imagewise exposure for obtaining a dye image and are not essentially developed during development. These silver halide grains are preferably not fogged in advance.

In the fine grain silver halide, the content of silver bromide is 0 to 100 mol%, and silver chloride and/or silver iodide may be added if necessary. The fine grain silver halide preferably contains 0.5 to 10 mol% of silver iodide.

The average grain size (average value of an equivalent-circle diameter of a projected area) of the fine grain silver halide is preferably 0.01 to 0.5 $\mu$m, and more preferably 0.02 to 0.2 $\mu$m.

The fine grain silver halide can be prepared following the same procedures as for a common photosensitive silver halide. In this case, the surface of each silver halide grain need not be optically sensitized nor spectrally sensitized. However, before the silver halide grains are added to a coating solution, it is preferable to add a well-known stabilizer such as a triazole-based compound, an azaindene-based compound, a benzothiazolium-based compound, a mercapto-based compound, or a zinc compound. Colloidal silver can be preferably added to this fine grain silver halide grain-containing layer.

The silver coating amount of the photosensitive material of the present invention is preferably 6.0 g/m$^2$ or less, and most preferably 4.5 g/m$^2$ or less.

Well-known photographic additives usable in the present invention are also described in the three Research Disclosures described above, and they are summarized in the following table.

| Additives | RD17643 | RD18716 | RD307105 |
| --- | --- | --- | --- |
| 1. Chemical sensitizers | page 23 | page 648; right column | page 866 |
| 2. Sensitivity increasing agents | | page 648; right column | |
| 3. Spectral sensitizers, super sensitizers | pages 23–24 | page 648, right column to page 649, right column | pages 866 to 868 |
| 4. Brighteners | page 24 | | page 868 |
| 5. Antifoggants and stabilizers | pages 24–25 | page 649, right column | pages 868 to 870 |
| 6. Light absorbent, filter dye, ultraviolet absorbents | pages 25–26 | page 649, right column to page 650, left column | page 873 |
| 7. Stain preventing agents | page 25, right column | page 650, left to right columns | page 872 |
| 8. Dye image stabilizer | page 25 | page 650, left column | page 872 |
| 9. Hardening agents | page 26 | page 651, left column | pages 874 to 875 |
| 10. Binder | page 26 | page 651, left column | pages 873 to 874 |
| 11. Plasticizers, lubricants | page 27 | page 650, right column | page 876 |
| 12. Coating aids, surface active agents | pages 26–27 | page 650, right column | pages 875 to 876 |
| 13. Antistatic agents | page 27 | page 650, right column | pages 876 to 877 |
| 14. Matting agent | | | pages 878 to 879 |

In order to prevent deterioration in photographic performance caused by formaldehyde gas, the photosensitive material is preferably added with a compound described in U.S. Pat. No. 4,411,987 or 4,435,503, which can react with formaldehyde to fix it.

The photosensitive material of the present invention preferably contains mercapto compounds described in U.S. Pat. Nos. 4,740,454 and 4,788,132, JP-A-62-18539, and JP-A-1-283551.

The photosensitive material of the present invention preferably contains a compound described in JP-A-1-106052, which releases a fogging agent, a development accelerator, a silver halide solvent, or a precursor of any of them regardless of a developed amount of silver produced by development.

The photosensitive material of the present invention preferably contains dyes dispersed by methods described in WO 04794/88 and PCT No. 1-502912, or dyes described in EP 317,308A, U.S. Pat. No. 4,420,555, and JP-A-1-259358.

Various color couplers can be used in the present invention, and specific examples of these couplers are described in patents described in above-mentioned Research Disclosure (RD), No. 17643, VII-C to VII-G and No. 307105, VII-C to VII-G.

Preferred examples of a yellow coupler are described in, e.g., U.S. Pat. Nos. 3,933,501, 4,022,620, 4,326,024, 4,401, 752, and 4,248,961, JP-B-58-10739, British Patents 1,425, 020 and 1,476,760, U.S. Pat. Nos. 3,973,968, 4,314,023, and 4,511,649, and EP 249,473A.

Examples of a magenta coupler are preferably 5-pyrazolone and pyrazoloazole compounds, and more preferably, compounds described in, e.g., U.S. Pat. Nos. 4,310,619 and 4,351,897, EP 73,636, U.S. Pat. Nos. 3,061, 432 and 3,725,067, Research Disclosure No. 24220 (June 1984), JP-A-60-33552, Research Disclosure No. 24230 (June 1984), JP-A-60-43659, JP-A-61-72238, JP-A-60-35730, JP-A-55-118034, and JP-A-60-185951, U.S. Pat. Nos. 4,500,630, 4,540,654, and 4,565,630, and WO No. 88/04795.

Examples of a cyan coupler are phenol and naphthol couplers, and preferably, those described in, e.g., U.S. Pat. Nos. 4,052,212, 4,146,396, 4,228,233, 4,296,200, 2,369, 929, 2,801,171, 2,772,162, 2,895,826, 3,772,002, 3,758,308, 4,343,011, and 4,327,173, West German Patent Application (OLS) No. 3,329,729, EP 121,365A and 249,453A, U.S. Pat. Nos. 3,446,622, 4,333,999, 4,775,616, 4,451,559, 4,427, 767, 4,690,889, 4,254,212, and 4,296,199, and JP-A-61-42658. In addition, it is also possible to use pyrazoloazole couplers described in JP-A-64-553, JP-A-64-554, JP-A-64-555, and JP-A-64-556 or an imidazole coupler described in U.S. Pat. No. 4,818,672.

Typical examples of a polymerized dye-forming coupler are described in U.S. Pat. Nos. 3,451,820, 4,080,221, 4,367, 288, 4,409,320, and 4,576,910, British Patent 2,102,173, and EP 341,188A.

Preferable examples of a coupler capable of forming colored dyes having proper diffusibility are those described in U.S. Pat. No. 4,366,237, British Patent 2,125,570, EP 96,570, and West German Patent Application (OLS) No. 3,234,533.

Preferable examples of a colored coupler for correcting, undesirable absorption of a colored dye are those described in Research Disclosure No. 17643, VII-G and No. 307105, VII-G, U.S. Pat. No. 4,163,670, JP-B-57-39413, U.S. Pat. Nos. 4,004,929 and 4,138,258, and British Patent 1,146,368. A coupler for correcting undesirable absorption of a colored dye by a fluorescent dye released upon coupling described in U.S. Pat. No. 4,774,181 or a coupler having a dye precursor group which can react with a developing agent to form a dye as a split-off group described in U.S. Pat. No. 4,777,120 may be preferably used.

Couplers releasing a photographically useful group upon coupling are preferably used in the present invention. DIR couplers, i.e., couplers releasing a development inhibitor are described in the patents cited in the above-described RD No. 17643, VII-F, RD No. 307105, VII-F, JP-A-57-151944, JP-A-57-154234, JP-A-60-184248, JP-A-63-37346, JP-A-63-37350, and U.S. Pat. Nos. 4,248,962 and 4,782,012.

Bleaching accelerator releasing couplers described in, e.g., RD Nos. 11449 and 24241 and JP-A-61-201247 can be effectively used to reduce a time required for a treatment having a bleaching function. This effect is notable especially when the coupler is added to a photosensitive material using the tabular silver halide grains described above.

Preferable examples of a coupler for imagewise releasing a nucleating agent or a development accelerator are described in British Patents 2,097,140 and 2,131,188, JP-A-59-157638, and JP-A-59-170840. It is also preferable to use compounds described in JP-A-60-107029, JP-A-60-252340, JP-A-1-44940, and JP-A-1-45687, which release, e.g., a fogging agent, a development accelerator, or a silver halide solvent upon a redox reaction with an oxidation product of a developing agent.

Examples of a coupler which can be used in the photosensitive material of the present invention are competing couplers described in, e.g., U.S. Pat. No. 4,130,427; polyequivalent couplers described in, e.g., U.S. Pat. Nos. 4,283,472, 4,338,393, and 4,310,618; a DIR redox compound releasing coupler, a DIR coupler releasing coupler, a DIR coupler releasing redox comound, or DIR redox releasing redox compounds described in, e.g., JP-A-60-185950 and JP-A-62-24252; couplers releasing a dye which turns to a colored form after being released described in EP 173,302A and 313,308A; a legand releasing coupler described in, e.g., U.S. Pat. No. 4,555,477; a coupler releasing a leuco dye described in JP-A-63-75747; and a coupler releasing a fluorescent dye described in U.S. Pat. No. 4,774,181.

The couplers for use in this invention can be added to the photosensitive material by various known dispersion methods.

Examples of a high-boiling organic solvent to be used in an oil-in-water dispersion method are described in, e.g., U.S. Pat. No. 2,322,027. Examples of the high-boiling organic solvent to be used in the oil-in-water dispersion method and having a boiling point of 175° C. or more at atmospheric pressure are phthalic esters (e.g., dibutyl phthalate, dicyclohexyl phthalate, di-2-ethylhexyl phthalate, decyl phthalate, bis(2,4-di-t-amylphenyl) phthalate, bis(2,4-di-t-amylphenyl) isophthalate, and bis(1,1-diethylpropyl) phthalate), phosphates or phosphonates (e.g., triphenyl phosphate, tricresyl phosphate, 2-ethylhexyl diphenyl phosphate, tricyclohexyl phosphate, tri-2-ethylhexyl phosphate, tridodecyl phosphate, tributoxyethyl phosphate, trichloropropyl phosphate, and di-2-ethylhexyl phenyl phosphonate), benzoates (e.g., 2-ethylhexyl benzoate, dodecyl benzoate, and 2-ethylhexyl p-hydroxybenzoate), amides (e.g., N,N-diethyldodecaneamide, N,N-diethyllaurylamide, and N-tetradecylpyrrolidone), alcohols or phenols (e.g., isostearyl alcohol and 2,4-di-tert-amylphenol), aliphatic carboxylates (e.g., bis(2-ethylhexyl) sebacate, dioctyl azelate, glycerol tributanoate, isostearyl lactate, and trioctyl citrate), aniline derivatives (e.g., N,N-dibutyl-2-butoxy-5-tert-octylaniline), and hydrocarbons (e.g., paraffin, dodecylbenzene, and diisopropylnaphthalene). An organic solvent having a boiling point of about 30° C. or more, and preferably, 50° C. to about 160° C. can be used as a co-solvent. Typical examples of the co-solvent are ethyl acetate, butyl acetate, ethyl propionate, methyl ethyl ketone, cyclohexanone, 2-ethoxyethyl acetate, and dimethylformamide.

Steps and effects of a latex dispersion method and examples of an impregnating latex are described in, e.g., U.S. Pat. No. 4,199,363 and West German Patent Application (OLS) Nos. 2,541,274 and 2,541,230.

Various types of an antiseptic agent or a mildewproofing agent are preferably added to the color photosensitive material of the present invention. Examples of the antiseptic agent and the mildewproofing agent are phenethyl alcohol, and 1,2-benzisothiazoline-3-one, n-butyl p-hydroxybenzoate, phenol, 4-chloro-3,5-dimethylphenol, 2-phenoxyethanol, and 2-(4-thiazolyl)benzimidazole described in JP-A-63-257747, JP-A-62-272248, and JP-A-1-80941.

The present invention can be applied to various color photosensitive materials. Examples of the material are a color negative film for a general purpose or a movie, a color reversal film for a slide or a television, color paper, a color positive film, and color reversal paper.

A support which can be suitably used in the present invention is described in, e.g., RD. No. 17643, page 28, RD. No. 18716, from the right column, page 647 to the left column, page 648, and RD. No. 307105, page 897.

In the photosensitive material of the present invention, the sum total of film thicknesses of all hydrophilic colloid layers on the side having emulsion layers is 28 $\mu$m or less, preferably 23 $\mu$m or less, more preferably 18 $\mu$m or less, and most preferably 16 $\mu$m or less. A film swell speed $T_{1/2}$ is preferably 30 sec. or less, and more preferably, 20 sec. or less. The film thickness means a film thickness measured under moisture conditioning at a temperature of 25° C. and a relative humidity of 55% (two days). The film swell speed $T_{1/2}$ can be measured in accordance with a known method in this field of art. For example, the film swell speed $T_{1/2}$ can be measured by using a swell meter described in Photogr. Sci Eng., A. Green et al., Vol. 19, No. 2, pp. 124 to 129. When 90% of a maximum swell film thickness reached by performing a treatment by using a color developing agent at 30° C. for 3 min. and 15 sec. is defined as a saturated film thickness, $T_{1/2}$ is defined as a time required for reaching $_{1/2}$ of the saturated film thickness.

The film swell speed $T_{1/2}$ can be adjusted by adding a film hardening agent to gelatin as a binder or changing aging conditions after coating. A swell ratio is preferably 150% to 400%. The swell ratio is calculated from the maximum swell film thickness measured under the above conditions in accordance with a relation : (maximum swell film thickness—film thickness)/film thickness.

In the photosensitive material of the present invention, hydrophilic colloid layers (called back layers) having a total dried film thickness of 2 to 20 $\mu$m are preferably formed on the side opposite to the side having emulsion layers. The back layers preferably contain, e.g., the light absorbent, the filter dye, the ultraviolet absorbent, the antistatic agent, the film hardener, the binder, the plasticizer, the lubricant, the coating aid, and the surfactant described above. The swell ratio of the back layers is preferably 150% to 500%.

The color photographic photosensitive material according to the present invention can be developed by conventional methods described in RD. No. 17643, pp. 28 and 29, RD. No. 18716, page 615, the left to right columns, and RD No. 307105, pp. 880 and 881.

A color developer used in development of the photosensitive material of the present invention is preferably an aqueous alkaline solution mainly consisting of an aromatic primary amine-based color developing agent. As this color developing agent, although an aminophenol-based compound is effective, a p-phenylenediamine-based compound is preferably used. Typical examples of the p-phenylenediamine-based compound are 3-methyl-4-amino-N,N-diethylaniline, 3-methyl-4-amino-N-ethyl-N-$\beta$-hydroxyethylaniline, 3-methyl-4-amino-N-ethyl-N-$\beta$-methanesulfonamidoethylani line, 3-methyl-4-amino-N-ethyl-N-$\beta$-methoxyethylaniline, and sulfates, hydrochlorides and p-toluenesulfonates thereof. Of these compounds, 3-methyl-4-amino-N-ethyl-N-$\beta$-hydroxyethylaniline sulfate is most preferred. These compounds can be used in a combination of two or more thereof in accordance with the application.

In general, the color developer contains a pH buffering agent such as a carbonate, a borate, or a phosphate of an alkali metal, and a development restrainer or an antifoggant such as a chloride, a bromide, an iodide, a benzimidazole, a benzothiazole, or a mercapto compound. If necessary, the color developer may also contain a preservative such as hydroxylamine, diethylhydroxylamine, a sulfite, a hydrazine, e.g., N,N-bis (carboxymethyl) hydrazine, a phenylsemicarbazide, triethanolamine, or a catechol sulfonate; an organic solvent such as ethylene glycol or diethylene glycol; a development accelerator such as benzyl alcohol, polyethylene glycol, a quaternary ammonium salt or an amine; a dye forming coupler; a competing coupler;

an auxiliary developing agent such as 1-phenyl-3-pyrazolidone; a viscosity imparting agent; and a chelating agent such as aminopolycarboxylic acid, an aminopolyphosphonic acid, an alkylphosphonic acid, or a phosphonocarboxylic acid. Examples of the chelating agent are ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N',N'-tetramethylenephosphonic acid, and ethylenediamine-di(o-hydroxyphenylacetic acid), and salts thereof.

In order to perform reversal development, black- and-white development is performed and then color development is performed. As a black-and-white developer, well-known black-and-white developing agents, e.g., a dihydroxybenzene such as hydroquinone, a 3-pyrazolidone such as 1-phenyl-3-pyrazolidone, and an aminophenyl such as N-methyl-p-aminophenol can be used singly or in a combination of two or more thereof. The pH of the color and black-and-white developers is generally 9 to 12. Although the quantity of replenisher of these developers depends on a color photographic photosensitive material to be processed, it is generally 3 liters or less per m$^2$ of the photosensitive material. The quantity of replenisher can be decreased to be 500 ml or less by decreasing a bromide ion concentration in the replenisher. In order to decrease the quantity of replenisher, a contact area of a processing tank with air is preferably decreased to prevent evaporation and oxidation of the replenisher upon contact with air.

A contact area of a photographic processing solution with air in a processing tank can be represented by an aperture defined below:

$$\text{Aperture} = \frac{\text{contact area (cm}^2\text{) of processing solution with air}}{\text{volume (cm}^3\text{) of processing solution}}$$

The above aperture is preferably 0.1 or less, and more preferably, 0.001 to 0.05. In order to reduce the aperture, a shielding member such as a floating cover may be provided on the liquid surface of the photographic processing solution in the processing tank. In addition, a method of using a movable cover described in JP-A-1-82033 or a slit developing method descried in JP-A-63-216050 may be used. The aperture is preferably reduced not only in color and black-and-white development steps but also in all subsequent steps, e.g., bleaching, bleach-fixing, fixing, washing, and stabilizing steps. In addition, a quantity of replenisher can be reduced by using a means of suppressing storage of bromide ions in the developer.

A color development time is normally two to five minutes. The processing time, however, can be shortened by setting a high temperature and a high pH and using the color developing agent at a high concentration.

The photographic emulsion layer is generally subjected to bleaching after color development. The bleaching may be performed either simultaneously with fixing (bleach-fixing) or independently thereof. In addition, in order to increase a processing speed, bleach-fixing may be performed after bleaching. Also, processing may be performed in a bleach-fixing bath having two continuous tanks, fixing may be performed before bleach-fixing, or bleaching may be performed after bleach-fixing, in accordance with the application. Examples of the bleaching agent are a compound of a multivalent metal such as iron(III); peroxides; quinones; and a nitro compound. Typical examples of the bleaching agent are an organic complex salt of iron(III), e.g., a complex salt of an aminopolycarboxylic acid such as ethylenediaminetetraacetic acid, diethylenetriaminepentaacetic acid, cyclohexanediaminetetraacetic acid, methyliminodiacetic acid, and 1,3-diaminopropanetetraacetic acid, and glycol ether diaminetetraacetic acid; or a complex salt of citric acid, tartaric acid, or malic acid. Of these compounds, an iron(III) complex salt of aminopolycarboxylic acid such as an iron (III) complex salt of ethylenediaminetetraacetic acid or 1,3-diaminopropanetetraacetic acid is preferred because it can increase a processing speed and prevent an environmental contamination. The iron(III) complex salt of aminopolycarboxylic acid is useful in both the bleaching and bleach-fixing solutions. The pH of the bleaching or bleach-fixing solution using the iron(III) complex salt of aminopolycarboxylic acid is normally 4.0 to 8. In order to increase the processing speed, however, processing can be performed at a lower pH.

A bleaching accelerator can be used in the bleaching solution, the bleach-fixing solution, and their pre-bath, if necessary. Useful examples of the bleaching accelerator are: compounds having a mercapto group or a disulfide group described in, e.g., U.S. Pat. No. 3,893,858, West German Patents 1,290,812 and 2,059,988, JP-A-53-32736, JP-A-53-57831, JP-A-53-37418, JP-A-53-72623, JP-A-53-95630, JP-A-53-95631, JP-A-53-104232, JP-A-53-124424, JP-A-53-141623, and JP-A-53-28426, and Research Disclosure No. 17,129 (July, 1978); a thiazolidine derivative described in JP-A-50-140129; thiourea derivatives described in JP-B-45-8506, JP-A-52-20832, JP-A-53-32735, and U.S. Pat. No. 3,706,561; iodides described in West German Patent 1,127, 715 and JP-A-58-16235; polyoxyethylene compounds descried in West German Patents 966,410 and 2,748,430; a polyamine compound described in JP-B-45-8836; compounds described in JP-A-49-40943, JP-A-49-59644, JP-A-53-94927, JP-A-54-35727, JP-A-55-26506, and JP-A-58-163940; and a bromide ion. Of these compounds, a compound having a mercapto group or a disulfide group is preferable since the compound has a large accelerating effect. In particular, compounds described in U.S. Pat. No. 3,893,858, West German Patent 1,290,812, and JP-A-53-95630 are preferred. A compound described in U.S. Pat. No. 4,552,834 is also preferable. These bleaching accelerators may be added in the photosensitive material. These bleaching accelerators are useful especially in bleach-fixing of a photographic color photosensitive material.

The bleaching solution or the bleach-fixing solution preferably contains, in addition to the above compounds, an organic acid in order to prevent a bleaching stain. The most preferable organic acid is a compound having an acid dissociation constant (pKa) of 2 to 5, e.g., acetic acid or propionic acid.

Examples of the fixing agent are thiosulfate, a thiocyanate, a thioether-based compound, a thiourea and a large amount of an iodide. Of these compounds, a thiosulfate, especially, ammonium thiosulfate can be used in the widest range of applications. In addition, a combination of thiosulfate and a thiocyanate, a thioether-based compound, or thiourea is preferably used. As a preservative of the fixing solution or the bleach-fixing solution, a sulfite, a bisulfite, a carbonyl bisulfite adduct, or a sulfinic acid compound described in EP 294,769A is preferred. In addition, in order to stabilize the fixing solution or the bleach-fixing solution, various types of aminopolycarboxylic acids or organic phosphonic acids are preferably added to the solution.

In the present invention, 0.1 to 10 mol/l of a compound having a pKa of 6.0 to 9.0 are preferably added to the fixing solution or the bleach-fixing solution in order to adjust the pH. Preferable examples of the compound are imidazoles such as imidazole, 1-methylimidazole, 1-ethylimidazole, and 2-methylimidazole.

The total time of a desilvering step is preferably as short as possible as long as no desilvering defect occurs. A preferable time is one to three minutes, and more preferably, one to two minutes. A processing temperature is 25° C. to 50° C., and preferably, 35° C. to 45° C. Within the preferable temperature range, a desilvering speed is increased, and generation of a stain after the processing can be effectively prevented.

In the desilvering step, stirring is preferably as strong as possible. Examples of a method of strengthening the stirring are a method of colliding a jet stream of the processing solution against the emulsion surface of the photosensitive material described in JP-A-62-183460, a method of increasing the stirring effect using rotating means described in JP-A-62-183461, a method of moving the photosensitive material while the emulsion surface is brought into contact with a wiper blade provided in the solution to cause turbulent flow on the emulsion surface, thereby improving the stirring effect, and a method of increasing the circulating flow amount in the overall processing solution. Such a stirring improving means is effective in any of the bleaching solution, the bleach-fixing solution, and the fixing solution. It is assumed that the improvement in stirring increases the speed of supply of the bleaching agent and the fixing agent into the emulsion film to lead to an increase in desilvering speed. The above stirring improving means is more effective when the bleaching accelerator is used, i.e., significantly increases the accelerating effect or eliminates fixing interference caused by the bleaching accelerator.

An automatic developing machine for processing the photosensitive material of the present invention preferably has a conveying means for a photosensitive material described in JP-A-60-191257, JP-A-191258, or JP-A-60-191259. As described in JP-A-60-191257, this conveying means can significantly reduce carry-over of a processing solution from a pre-bath to a post-bath, thereby effectively preventing degradation in performance of the processing solution. This effect significantly shortens especially a processing time in each processing step and reduces a quantity of replenisher for a processing solution.

The silver halide photographic photosensitive material of the present invention is normally subjected to washing and/or stabilizing steps after desilvering. An amount of water used in the washing step can be arbitrarily determined over a broad range in accordance with the properties of the photosensitive material, (e.g., a property dependent on a coupler used) the application of the material, the temperature of the water, the number of water tanks (the number of stages), a replenishing system, e.g., a counter or forward current, and other conditions. The relationship between the amount of water and the number of water tanks in a multi-stage counter-current system can be obtained by a method described in "Journal of the Society of Motion Picture and Television Engineering", Vol. 64, PP. 248–253 (May, 1955).

According to the multi-stage counter-current system described in the above literature, the amount of water used for washing can be greatly decreased. Since washing water stays in the tanks for a long period of time, however, bacteria multiply and floating substances may be undesirably attached to the photosensitive material. In order to solve this problem in the process of the color photographic photosensitive material of the present invention, a method of decreasing calcium and magnesium ions can be effectively utilized, as described in JP-A-62-288838. In addition, a germicide such as an isothiazolone compound and cyabendazole described in JP-A-57-8542, a chlorine-based germicide such as chlorinated sodium isocyanurate, and germicides such as benzotriazole described in Hiroshi Horiguchi et al., "Chemistry of Antibacterial and Antifungal Agents", (1986), Sankyo Shuppan, Eiseigijutsu-Kai ed., "Sterilization, Antibacterial, and Antifungal Techniques for Microorganisms", (1982), Kogyogijutsu-Kai, and Nippon Bokin Bokabi Gakkai ed., "Dictionary of Antibacterial and Antifungal Agents", (1986).

The pH of the water for washing the photosensitive material of the present invention is 4 to 9, and preferably, 5 to 8. The water temperature and the washing time can vary in accordance with the properties and applications of the photosensitive material. Normally, the washing time is 20 seconds to 10 minutes at a temperature of 15° C. to 45° C., and preferably, 30 seconds to 5 minutes at 25° C. to 40° C. The photosensitive material of the present invention can be processed directly by a stabilizing agent in place of washing. All known methods described in JP-A-57-8543, JP-A-58-14834, and JP-A-60-220345 can be used in such stabilizing processing.

Stabilizing is sometimes performed subsequently to washing. An example is a stabilizing bath containing a dye stabilizing agent and a surfactant to be used as a final bath of the photographic color photosensitive material. Examples of the dye stabilizing agent are an aldehyde such as formalin and glutaraldehyde, an N-methylol compound, hexamethylenetetramine, and an aldehyde bisulfite adduct. Various chelating agents or mildewproofing agents can be added in the stabilizing bath.

An overflow solution produced upon washing and/or replenishment of the stabilizing solution can be reused in another step such as a desilvering step.

In the processing using an automatic developing machine or the like, if each processing solution described above is condensed by evaporation, water is preferably added to correct condensation.

The silver halide color photosensitive material of the present invention may contain a color developing agent in order to simplify processing and increases a processing speed. For this purpose, various types of precursors of a color developing agent can be preferably used. Examples of the precursor are an indoaniline-based compound described in U.S. Pat. No. 3,342,597, Schiff base compounds described in U.S. Pat. No. 3,342,599 and Research Disclosure (RD) Nos. 14,850 and 15,159, an aldol compound described in RD No. 13,924, a metal salt complex described in U.S. Pat. No. 3,719,492, and an urethane-based compound described in JP-A-53-135628.

The silver halide color photosensitive material of the present invention may contain various 1-phenyl-3-pyrazolidones in order to accelerate color development, if necessary. Typical examples of the compound are described in JP-A-56-64339, JP-A-57-144547, and JP-A-58-115438.

Each processing solution in the present invention is used at a temperature of 10° C. to 50° C. Although a normal processing temperature is 33° C. to 38° C., processing may be accelerated at a higher temperature to shorten a processing time, or image quality or stability of a processing solution may be improved at a lower temperature.

The silver halide photosensitive material of the present invention can be applied to thermal development photosensitive materials described in, e.g., U.S. Pat. No. 4,500,626, JP-A-60-133449, JP-A-59-218443, JP-A-61-238056, and EP 210,660A2.

EXAMPLES

The present invention will be described in more detail below by way of its examples, but the present invention is not limited to these examples.

Example 1

A plurality of layers having the following compositions were coated on an undercoated cellulose triacetate support to form sample 101 as a multilayered color photosensitive material.

(Compositions of Photosensitive Layers)

Numerals corresponding to each component indicates a coating amount represented in units of g/m². The coating amount of a silver halide is represented by the coating amount of silver. The coating amount of a sensitizing dye is represented in units of mols per mol of a silver halide in the same layer.

(Sample 101)

Layer 1: Antihalation layer

| | | |
|---|---|---|
| Black colloidal silver | silver | 0.18 |
| Gelatin | | 0.80 |

Layer 2: Interlayer

| | |
|---|---|
| 2,5-di-t-pentadecylhydroquinone | 0.18 |
| EX-1 | 0.18 |
| EX-3 | 0.020 |
| EX-12 | $2.0 \times 10^{-3}$ |
| U-1 | 0.060 |
| U-2 | 0.080 |
| U-3 | 0.10 |
| HBS-1 | 0.10 |
| HBS-2 | 0.020 |
| Gelatin | 0.50 |

Layer 3: 1st red-sensitive emulsion layer

| | | |
|---|---|---|
| Emulsion A | silver | 0.25 |
| Emulsion B | silver | 0.25 |
| Sensitizing dye I | | $6.9 \times 10^{-5}$ |
| Sensitizing dye II | | $1.8 \times 10^{-5}$ |
| Sensitizing dye III | | $3.1 \times 10^{-4}$ |
| EX-2 | | 0.17 |
| EX-10 | | 0.007 |
| EX-14 | | 0.17 |
| C-1 | | 0.035 |
| U-1 | | 0.070 |
| U-2 | | 0.050 |
| U-3 | | 0.070 |
| HBS-1 | | 0.060 |
| Gelatin | | 0.87 |

Layer 4: 2nd red-sensitive emulsion layer

| | | |
|---|---|---|
| Emulsion G | silver | 1.00 |
| Sensitizing dye I | | $5.1 \times 10^{-5}$ |
| Sensitizing dye II | | $1.4 \times 10^{-5}$ |
| Sensitizing dye III | | $2.3 \times 10^{-4}$ |
| EX-2 | | 0.20 |
| EX-3 | | 0.050 |
| EX-10 | | 0.005 |
| EX-14 | | 0.20 |
| EX-15 | | 0.050 |
| C-1 | | 0.035 |
| U-1 | | 0.070 |
| U-2 | | 0.050 |
| U-3 | | 0.070 |
| Gelatin | | 1.10 |

Layer 5: 3rd red-sensitive emulsion layer

| | | |
|---|---|---|
| Emulsion D | silver | 1.60 |
| Sensitizing dye I | | $5.4 \times 10^{-5}$ |
| Sensitizing dye II | | $1.4 \times 10^{-5}$ |
| Sensitizing dye III | | $2.4 \times 10^{-4}$ |
| EX-2 | | 0.097 |
| EX-3 | | 0.010 |
| EX-4 | | 0.080 |
| C-1 | | 0.010 |
| HBS-1 | | 0.10 |
| HBS-2 | | 0.10 |
| Gelatin | | 1.10 |

Layer 6: Interlayer

| | |
|---|---|
| EX-5 | 0.040 |
| HBS-1 | 0.020 |
| Gelatin | 0.40 |

Layer 7: 1st green-sensitive emulsion layer

| | | |
|---|---|---|
| Emulsion A | silver | 0.15 |
| Emulsion B | silver | 0.15 |
| Sensitizing dye IV | | $3.0 \times 10^{-5}$ |
| Sensitizing dye V | | $1.0 \times 10^{-4}$ |
| Sensitizing dye VI | | $3.8 \times 10^{-4}$ |
| EX-1 | | 0.021 |
| EX-6 | | 0.26 |
| EX-7 | | 0.030 |
| EX-8 | | 0.025 |
| HBS-1 | | 0.10 |
| HBS-3 | | 0.010 |
| Gelatin | | 0.63 |

Layer 8: 2nd green-sensitive emulsion layer

| | | |
|---|---|---|
| Emulsion C | silver | 0.45 |
| Sensitizing dye IV | | $2.1 \times 10^{-5}$ |
| Sensitizing dye V | | $7.0 \times 10^{-5}$ |
| Sensitizing dye VI | | $2.6 \times 10^{-4}$ |
| EX-6 | | 0.094 |
| EX-7 | | 0.026 |
| EX-8 | | 0.018 |
| HBS-1 | | 0.16 |
| HBS-3 | | $8.0 \times 10^{-3}$ |
| Gelatin | | 0.50 |

Layer 9: 3rd green-sensitive emulsion layer

| | | |
|---|---|---|
| Emulsion E | silver | 0.20 |
| Sensitizing dye IV | | $3.5 \times 10^{-5}$ |
| Sensitizing dye V | | $8.0 \times 10^{-5}$ |
| Sensitizing dye VI | | $3.0 \times 10^{-4}$ |
| EX-1 | | 0.013 |
| EX-11 | | 0.065 |
| EX-13 | | 0.019 |
| HBS-1 | | 0.10 |
| HBS-2 | | 0.10 |
| Gelatin | | 1.10 |

Layer 10: Yellow filter layer

| | | |
|---|---|---|
| Yellow colloidal silver | silver | 0.050 |
| EX-5 | | 0.080 |
| HBS-1 | | 0.030 |
| Gelatin | | 0.35 |

Layer 11: 1st blue-sensitive emulsion layer

| | | |
|---|---|---|
| Emulsion A | silver | 0.080 |
| Emulsion B | silver | 0.070 |
| Emulsion F | silver | 0.070 |
| Sensitizing dye VII | | $3.5 \times 10^{-4}$ |
| EX-8 | | 0.042 |
| EX-9 | | 0.72 |
| HBS-1 | | 0.28 |
| Gelatin | | 1.10 |

-continued (Sample 101)

Layer 12: 2nd blue-sensitive emulsion layer

| | |
|---|---|
| Emulsion G | silver 0.45 |
| Sensitizing dye VII | $2.1 \times 10^{-4}$ |
| EX-9 | 0.15 |
| EX-10 | $7.0 \times 10^{-3}$ |
| HBS-1 | 0.050 |
| Gelatin | 0.78 |

Layer 13: 3rd blue-sensitive emulsion layer

| | |
|---|---|
| Emulsion H | silver 0.77 |
| Sensitizing dye VII | $2.2 \times 10^{-4}$ |
| EX-9 | 0.20 |
| HBS-1 | 0.070 |
| Gelatin | 0.69 |

Layer 14: 1st protective layer

| | |
|---|---|
| Emulsion I | silver 0.20 |
| U-4 | 0.11 |
| U-5 | 0.17 |
| HBS-1 | $5.0 \times 10^{-2}$ |
| Gelatin | 0.50 |

Layer 15: 2nd protective layer

| | |
|---|---|
| H-1 | 0.40 |
| B-1 (diameter = 1.7 $\mu$m) | $5.0 \times 10^{-2}$ |
| B-2 (diameter = 1.7 $\mu$m) | 0.10 |
| B-3 | 0.10 |
| S-1 | 0.20 |
| Gelatin | 0.80 |

In addition, in order to improve storage stability, processability, a resistance to pressure, antiseptic and mildewproofing properties, antistatic properties, and coating properties, W-1, W-2, W-3, B-4, B-5, F-1, F-2, F-3, F-4, F-5, F-6, F-7, F-8, F-9, F-10, F-11, F-12, F-13, iron salt, lead salt, gold salt, platinum salt, iridium salt, and rhodium salt were added to all of the above layers.

(Samples 102–113)

Samples 102 to 113 were formed by replacing the coupler C-1 added to the layers 3, 4, and 5 of the sample 101 with couplers for comparison and couplers of the present invention. Table 1 shows the types and amounts (represented by molar ratio when C-1 is set 1.0) of the added couplers. These addition amounts were determined such that the same gradation (gamma) was obtained.

These samples were exposed imagewise with white light and subjected to the following color development. The results of the obtained photographic performance are listed in Table 1.

The sharpness was measured by a conventional MTF method following the same procedures as described above. In addition, after the samples were similarly exposed imagewise with white light, they were left to stand under forced conditions at a temperature of 50° C. and a relative humidity of 80% for 10 days. Thereafter, development was performed following the same procedures as described above. Also, after imagewise exposure was performed through a red filter (SC-62 available from Fuji Photo Film Co., Ltd.), uniform exposure at 0.02 CMS was performed through a green filter (BPN-45 available from Fuji Photo Film Co., Ltd.), and then development was performed. Values obtained by subtracting a magenta density at a cyan fog density from a magenta density at a cyan density of 1.5 are shown as a color turbidity in Table 1.

Furthermore, soft X-rays were radiated through apertures of 500 $\mu$m×0.4 mm and 15 $\mu$m×0.4 mm, and then color development was preformed following the same procedures as described above. A cyan color forming density ratio at the center of each image was evaluated as an edge effect. The result is also shown in Table 1.

TABLE 1

| Sample | | Couplers of layers 3, 4 and 5 Type | Amount | MTF value 25 cycle/mm cyan image | Color turbidity | 50° C. 80% after 10 days Fog change* | Sensitivity change* | Edge effect |
|---|---|---|---|---|---|---|---|---|
| 101 | (Comparative Example) | C-1 | 0.1 | 0.63 | −0.04 | +0.07 | −0.15 | 1.38 |
| 102 | (Comparative Example) | C-2 | 1.2 | 0.64 | −0.05 | +0.06 | −0.13 | 1.39 |
| 103 | (Comparative Example) | C-3 | 0.60 | 0.58 | 0.00 | +0.06 | −0.13 | 1.32 |
| 104 | (Comparative Example) | C-4 | 0.80 | 0.60 | −0.04 | +0.07 | −0.16 | 1.35 |
| 105 | (Comparative Example) | C-5 | 0.30 | 0.62 | −0.04 | +0.05 | −0.13 | 1.37 |
| 106 | (Comparative Example) | C-6 | 2.5 | 0.59 | −0.01 | +0.05 | −0.12 | 1.33 |
| 107 | (Present Invention) | (7) | 0.30 | 0.70 | −0.09 | +0.02 | −0.05 | 1.52 |
| 108 | (Present Invention) | (8) | 0.50 | 0.69 | −0.07 | +0.03 | −0.06 | 1.50 |
| 109 | (Present Invention) | (10) | 0.50 | 0.69 | −0.07 | +0.04 | −0.07 | 1.49 |
| 110 | (Present Invention) | (14) | 0.40 | 0.71 | −0.09 | +0.02 | −0.05 | 1.52 |
| 111 | (Present Invention) | (28) | 0.30 | 0.71 | −0.09 | +0.02 | −0.04 | 1.53 |
| 112 | (Present Invention) | (31) | 0.50 | 0.71 | −0.09 | +0.02 | −0.04 | 1.52 |

TABLE 1-continued

| Sample | Couplers of layers 3, 4 and 5 | | MTF value 25 cycle/mm cyan image | 50° C. 80% after 10 days | | | Edge effect |
|---|---|---|---|---|---|---|---|
| | Type | Amount | | Color turbidity | Fog change* | Sensitivity change* | |
| 113 (Present Invention) | (44) | 0.30 | 0.71 | −0.09 | +0.02 | −0.04 | 1.53 |

*A fog change in cyan density. An increase is represented by +.
**A relative value of a logarithm of an exposure amount of a cyan density (fog +0.2). An increase is represented by +.

The color development was performed using an automatic developing machine in accordance with the following method (until the accumulated quantity of a replenisher became three times the volume of a corresponding mother solution tank).

Processing Method

| Process | Time | Temperature | Quantity of replenisher* | Tank volume |
|---|---|---|---|---|
| Color development | 3 min. 15 sec. | 38° C. | 33 ml | 20 l |
| Bleaching | 6 min. 30 sec. | 38° C. | 25 ml | 40 l |
| Washing | 2 min. 10 sec. | 24° C. | 1,200 ml | 20 l |
| Fixing | 4 min. 20 sec. | 38° C. | 25 ml | 30 l |
| Washing (1) | 1 min. 05 sec. | 24° C. | Counter flow piping from (2) to (1) | 10 l |
| Washing (2) | 1 min. 00 sec. | 24° C. | 1,200 ml | 10 l |
| Stabilization | 1 min. 05 sec. | 38° C. | 25 ml | 10 l |
| Drying | 4 min. 20 sec. | 55° C. | | |

*A quantity of replenisher is a quantity per meter of a 35-mm wide sample

The compositions of the processing solutions will be presented below.

| | Mother solution (g) | Replenisher (g) |
|---|---|---|
| Color developing solution: | | |
| Diethylenetriaminepentaacetic acid | 1.0 | 1.1 |
| 1-hydroxyethylidene-1,1-diphosphonic acid | 3.0 | 3.2 |
| Sodium sulfite | 4.0 | 4.4 |
| Potassium carbonate | 30.0 | 37.0 |
| Potassium bromide | 1.4 | 0.7 |
| Potassium iodide | 1.5 mg | — |
| Hydroxylamine sulfate | 2.4 | 2.8 |
| 4-[N-ethyl-N-β-hydroxylethylamino]-2-methylaniline sulfate | 4.5 | 5.5 |
| Water to make | 1.0 l | 1.0 l |
| pH | 10.5 | 10.10 |
| Bleaching solution: | | |
| Ferric sodium ethylenediaminetetraacetate trihydrate | 100.0 | 120.0 |
| Disodium ethylenediaminetetraacetate | 10.0 | 10.0 |
| Ammonium bromide | 140.0 | 160.0 |
| Ammonium nitrate | 30.0 | 35.0 |
| Ammonia water (27%) | 6.5 ml | 4.0 ml |
| Water to make | 1.0 l | 1.0 l |
| pH | 6.0 | 5.7 |
| Fixing solution: | | |
| Disodium ethylenediaminetetraacetate | 0.5 | 0.7 |
| Sodium sulfite | 7.0 | 8.0 |
| Sodium bisulfite | 5.0 | 5.5 |

| | Mother solution (g) | Replenisher (g) |
|---|---|---|
| Ammonium thiosulfate aqueous solution (70%) | 170.0 ml | 200.0 ml |
| Water to make | 1.0 l | 1.0 l |
| pH | 6.7 | 6.6 |
| Stabilizing solution: | | |
| Formalin (37%) | 2.0 ml | 3.0 ml |
| Polyoxyethylene p-monononylphenyl ether (average degree of polymetrization = 10) | 0.3 | 0.45 |
| Disodium ethylenediaminetetraacetate | 0.05 | 0.08 |
| Water to make | 1.0 | 1.0 |
| pH | 5.0–8.0 | 5.0–8.0 |

As is apparent from Table 1, each sample of the present invention is excellent in color reproducibility represented by the color turbidity and in sharpness represented by the MTF value and the edge effect. In addition, each sample of the present invention is preferable in that a variation in its photographic performance is small under the forced conditions of 50° C. and 80%.

Example 2

0.010, 0.015, and 0.007 g/m² of coupler (44) of the present invention were added to the layers 3, 4, and 5, respectively, of the sample 105 of JP-A-2-44344, and 0.012 and 0.014 g/m² of coupler (15) of the present invention were added to its layers 7 and 9, respectively, thereby forming a sample 201. Samples 202, 203, and 204 were formed by replacing the coupler (15) of the layers 7 and 9 of the sample 201 with equal molar quantities of couplers (34), (36), and (79), respectively. 0.010 g/m² of coupler (28) of the present invention was added to the layer 11 of the sample 204 to form a sample 205. Samples 206 and 207 were formed by replacing the coupler (28) of the sample 205 with equal molar quantities of couplers (44) and (6), respectively.

These samples were irradiated with X-rays for edge effect evaluation as in Example 1 and subjected to the following color development, thereby evaluating the edge effect of a cyan image. The result is shown in Table 2. As can be seen from Table 2, each sample of the present invention is excellent in sharpness represented by the edge effect.

TABLE 2

| Sample | | Couplers of present invention | Edge effect |
|---|---|---|---|
| 105* | (Comparative Example) | — | 1.32 |

TABLE 2-continued

| Sample | | Couplers of present invention | Edge effect |
|---|---|---|---|
| 201 | (Present Invention) | (44) (15) | 1.48 |
| 202 | (Present Invention) | (44) (34) | 1.48 |
| 203 | (Present Invention) | (44) (36) | 1.50 |
| 204 | (Present Invention) | (44) (39) | 1.50 |
| 205 | (Present Invention) | (44) (39) (28) | 1.52 |
| 206 | (Present Invention) | (44) (39) | 1.53 |
| 207 | (Present Invention) | (44) (39) (6) | 1.51 |

*Sample 105 of JP-A-2-44344

Processing Method

| Process | Time | Temperature | Quantity of replenisher* | Tank volume |
|---|---|---|---|---|
| Color development | 3 min. 15 sec. | 37.8° C. | 25 ml | 10 l |
| Bleaching | 45 sec. | 38° C. | 5 ml | 4 l |
| Bleach-fixing (1) | 45 sec. | 38° C. | — | 4 l |
| Bleach-fixing (2) | 45 sec. | 38° C. | 30 ml | 4 l |
| Washing (1) | 20 sec. | 38° C. | — | 2 l |
| Washing (2) | 20 sec. | 38° C. | 30 ml | 2 l |
| Stabilization | 20 sec. | 38° C. | 20 ml | 2 l |
| Drying | 1 min. | 55° C. | | |

*A quantity of replenisher is a quantity per meter of a 35-mm wide sample

Each of the bleach-fixing and washing steps was performed by a counter flow system piping from (2) to (1), and all of an overflow solution of the bleaching solution was introduced to the bleach-fixing step (2).

In the above processing, an amount of the bleach-fixing solution carried over to the washing step was 2 ml per meter of a 35-mm wide photosensitive material.

| | Mother solution (g) | Replenisher (g) |
|---|---|---|
| Color developing solution: | | |
| Diethylenetriamine-pentaacetic acid | 5.0 | 6.0 |
| Sodium sulfite | 4.0 | 5.0 |
| Potassium carbonate | 30.0 | 37.0 |
| Potassium bromide | 1.3 | 0.5 |
| Potassium iodide | 1.2 mg | — |
| Hydroxylamine sulfate | 2.0 | 3.6 |
| 4-[N-ethyl-N-β-hydroxylethylamino]-2-methylaniline sulfate | 4.7 | 6.2 |
| Water to make | 1.0 l | 1.0 l |
| pH | 10.00 | 10.15 |

| | Mother solution (g) | Replenisher (g) |
|---|---|---|
| Bleaching solution: | | |
| Ferric ammonium 1,3-diaminopropane-tetraacetate monohydrate | 144.0 | 206.0 |
| 1,3-diaminopropane-tetraacetic acid | 2.8 | 4.0 |
| Ammonium bromide | 84.0 | 120.0 |
| Ammonium nitrate | 17.5 | 25.0 |
| Ammonia water (27%) | 10.0 ml | 1.8 ml |
| Acetic acid (98%) | 51.1 | 73.0 |
| Water to make | 1.0 l | 1.0 l |
| pH | 4.3 | 3.4 |
| Bleach-fixing solution: | | |
| Ferric ammonium ethylenediamine-tetraacetate dihydrate | 50.0 | — |
| Disodium ethylene-diaminetetraacetate | 5.0 | 25.0 |
| Ammonium sulfite | 12.0 | 20.0 |
| Ammonium thiosulfate aqueous solution (700 g/l) | 290.0 ml | 320.0 ml |
| Ammonia water (27%) | 6.0 ml | 15.0 ml |
| Water to make | 1.0 l | 1.0 l |
| pH | 6.8 | 8.0 |

Washing Solution: Common for Mother Solution and Replenisher

Tap water was supplied to a mixed-bed column filled with an H type strongly acidic cation exchange resin (Amberlite IR-120B: available from Rohm & Haas Co.) and an OH type strongly basic anion exchange resin (Amberlite IR-400: available from Rohm & Haas Co.) to set the concentrations of calcium and magnesium to be 3 mg/l or less. Subsequently, 20 mg/l of sodium isocyanuric dichloride and 150 mg/l of sodium sulfate were added. The pH of the solution fell within the range of 6.5 to 7.5.

| Stabilizing solution: | Common for mother solution and replenisher (g) |
|---|---|
| Formalin (37%) | 1.2 ml |
| Surfactant [$C_{10}H_{21}$—O—$(CH_2CH_2O)_{10}$—H] | 0.4 |
| Ethylene glycol | 1.0 |
| Water to make | 1.0 l |
| pH | 5.0–7.0 |

Example 3

0.035 g/m$^2$ of coupler (44) of the present invention, 0.018 g/m$^2$ of coupler (36) of the present invention, and 0.022 g/m$^2$ of coupler (6) of the present invention were added to layers 3, 7, and 13, respec- tively, of the photosensitive material 10 described in Example 3 of JP-A-2-93641, thereby forming a sample 301. When the evaluation was performed following the same procedures as in Example 1, it was confirmed that the sample 301 was superior to the photosensitive material 10 of the above-mentioned patent application in sharpness, color reproducibility, and photosensitive material storage stability.

The compounds used in the present invention are as follows.

EX-1
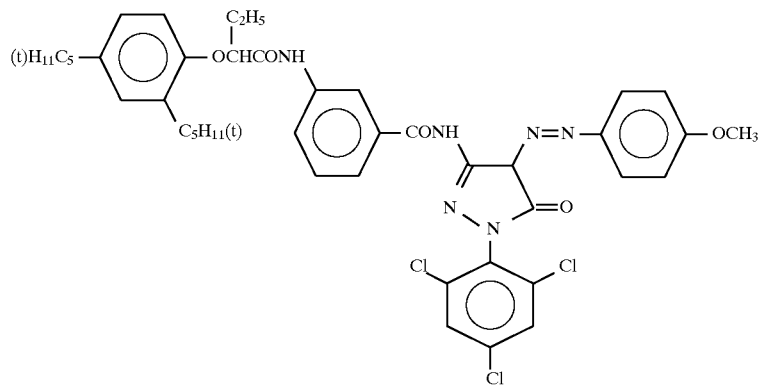
EX-2
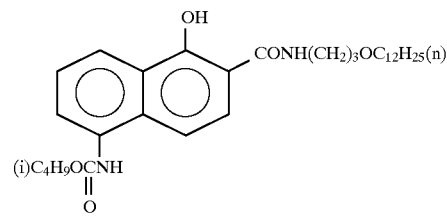
EX-3
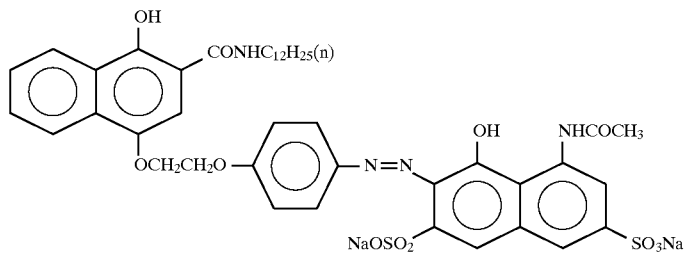
EX-4
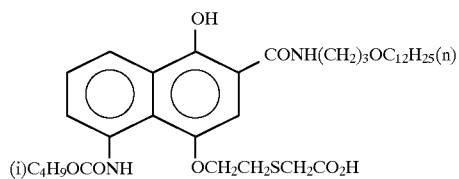
EX-5
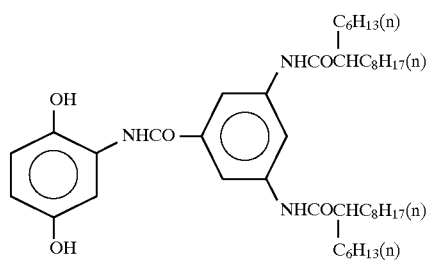
EX-6
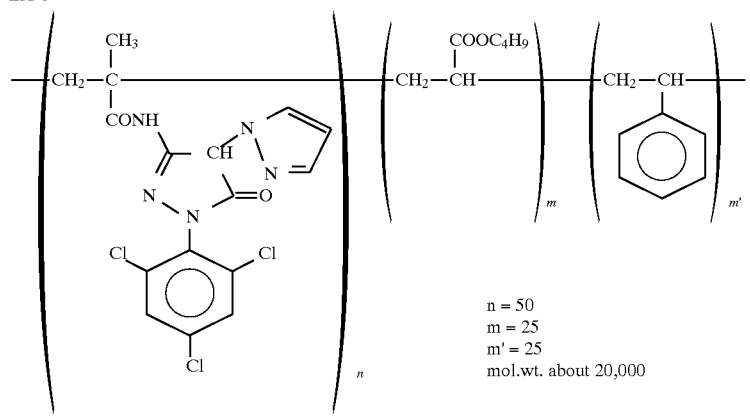
$n = 50$
$m = 25$
$m' = 25$
mol.wt. about 20,000

EX-7
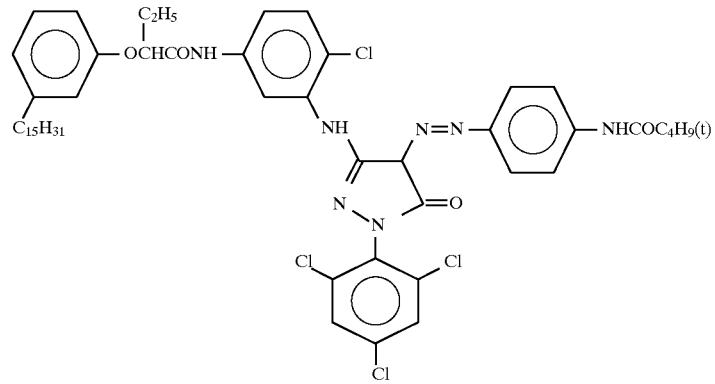
EX-8
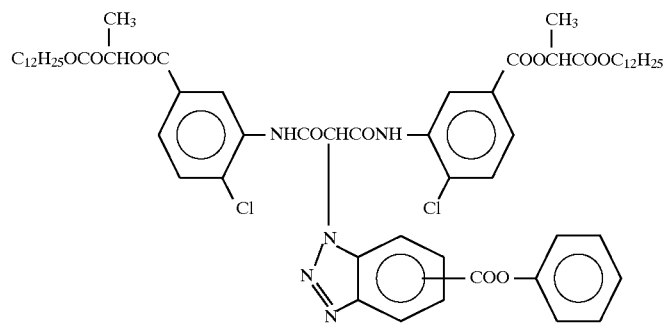
EX-9
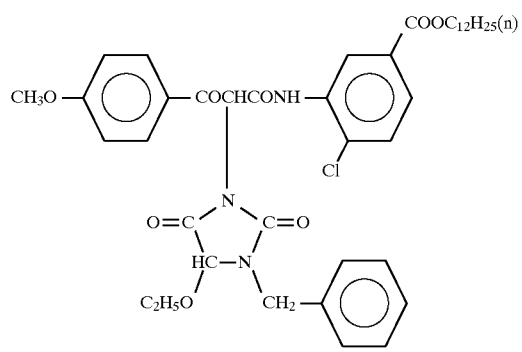
EX-10
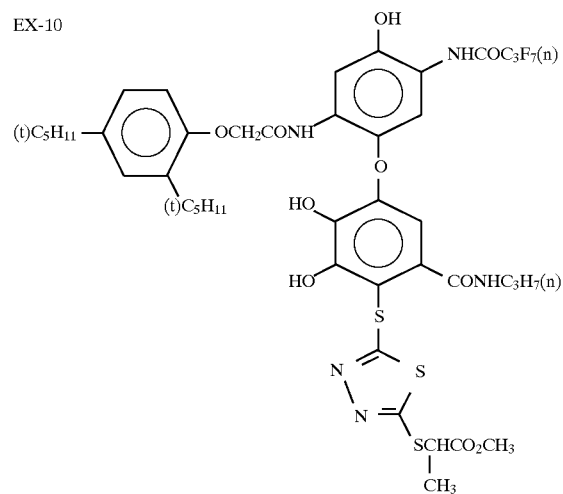
EX-11
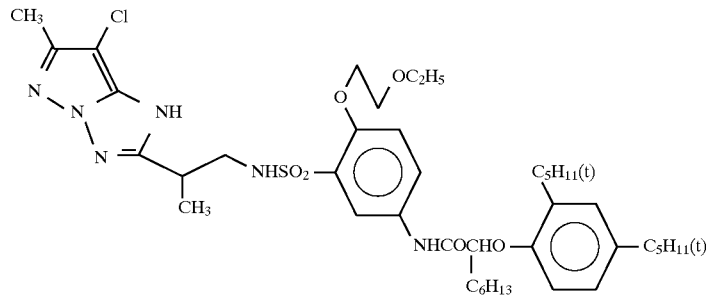

-continued
EX-12
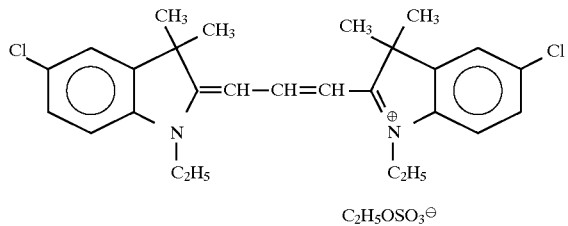
EX-13
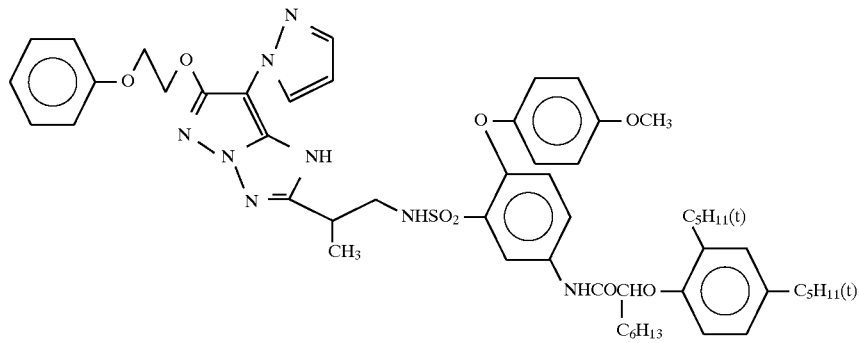
EX-14
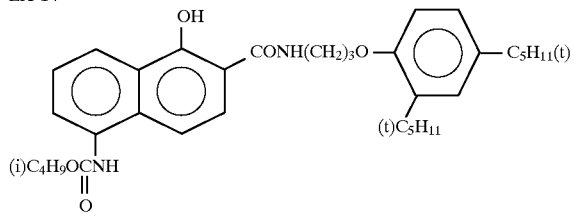
EX-15
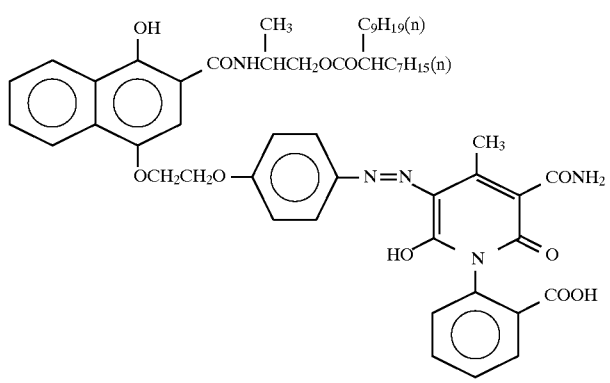
U-1
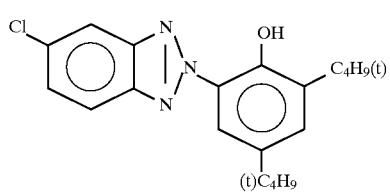
U-2
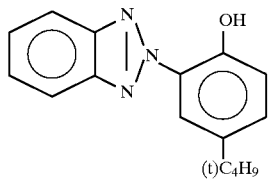

U-3
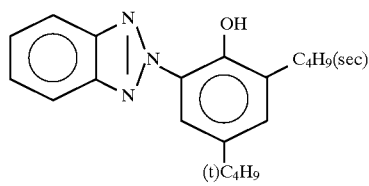
U-4
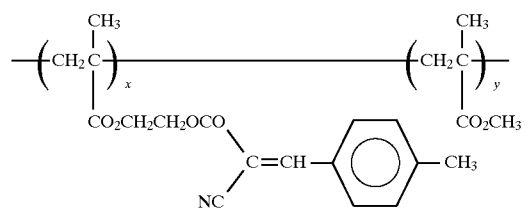
U-5
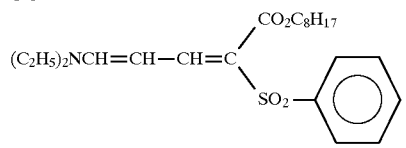
HBS-1
tricresyl phosphate
HBS-2
di-n-butyl phthalate
HBS-3
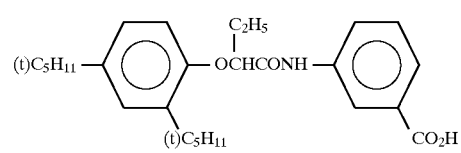
Sensitizing dye I
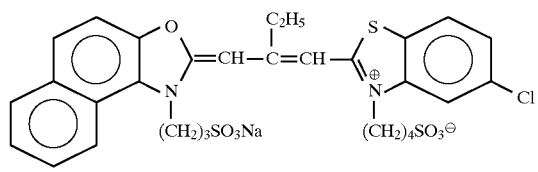
Sensitizing dye II
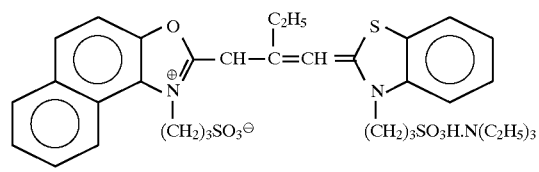
Sensitizing dye III
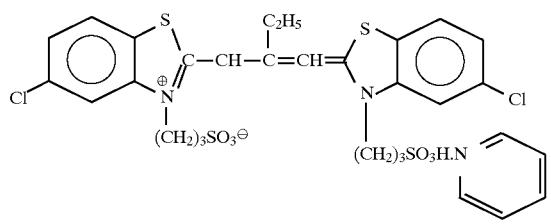
Sensitizing dye IV
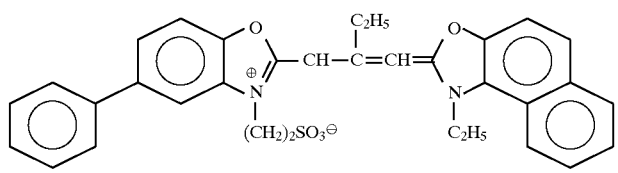
Sensitizing dye V
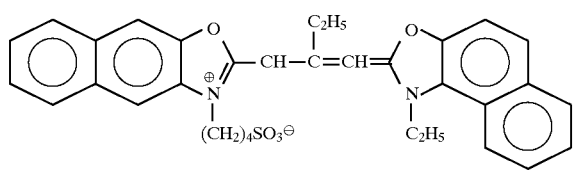

-continued
Sensitizing dye VI
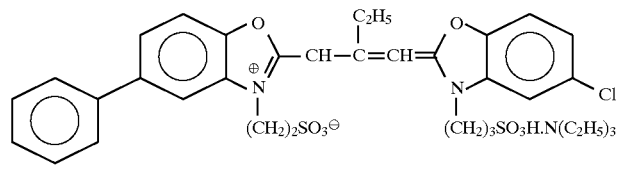
Sensitizing dye VII
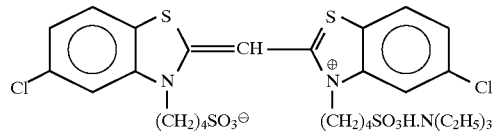
S-1
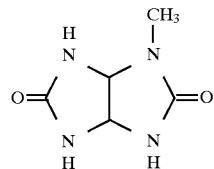
H-1
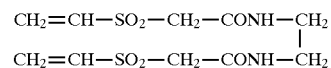
B-1
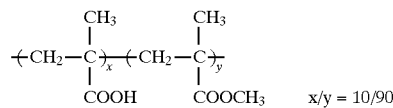   x/y = 10/90
B-2
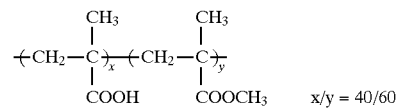   x/y = 40/60
B-3
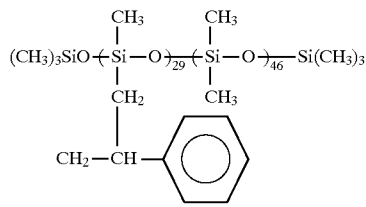
B-4
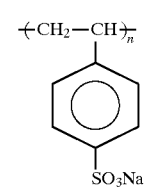
B-5
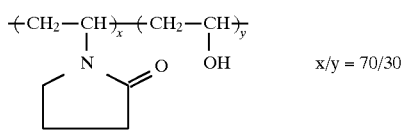   x/y = 70/30
W-1
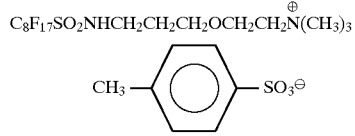
W-2
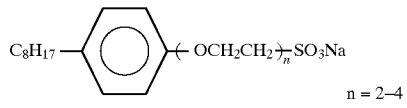   n = 2–4
W-3
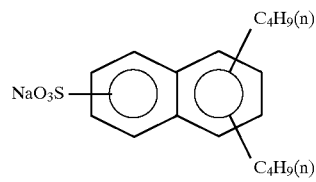

-continued
F-1
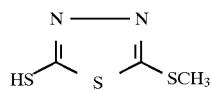
F-2
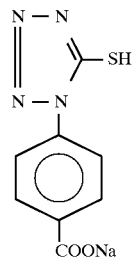
F-3
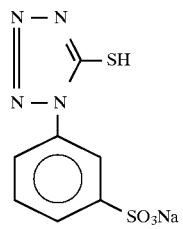
F-4
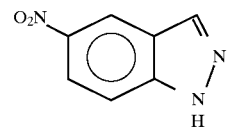
F-5
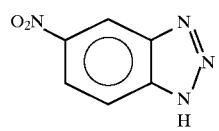
F-6
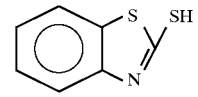
F-7
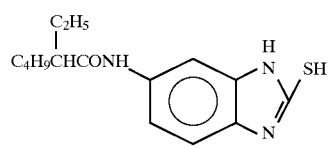
F-8
F-9
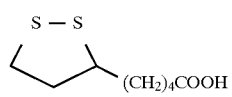
F-10
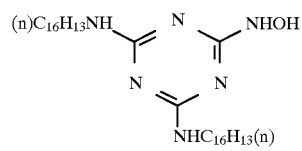
F-11
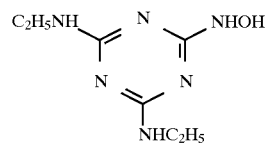
F-12
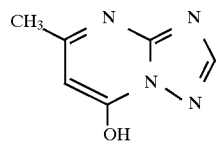
F-13
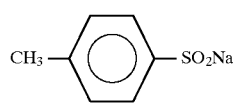

-continued
C-1 (Coupler (19) of JP-A-60-218645)
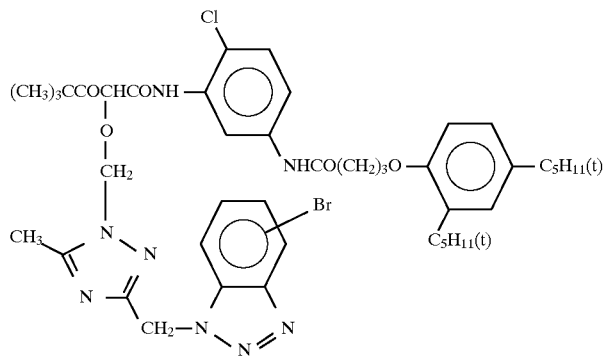
C-2 (Coupler (1) of JP-A-60-249148)
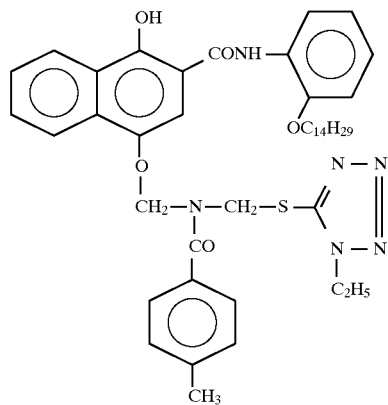
C-3 (Coupler (26) of JP-A-61-156127)
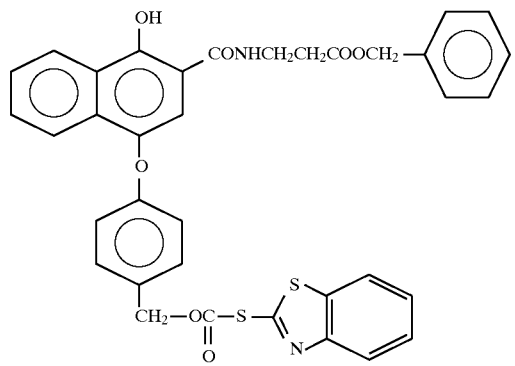

-continued
C-4 (Compound 5 of U.S. Pat. No. 4,861,701)

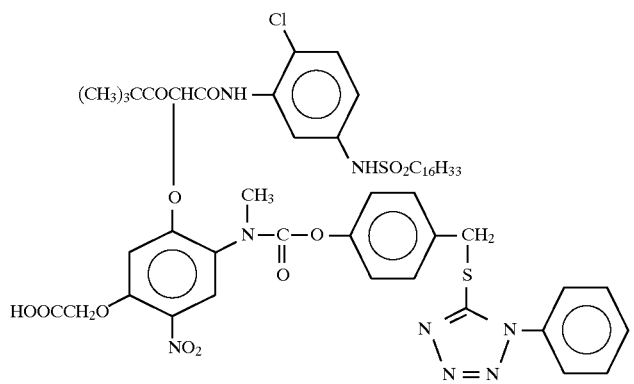

C-5 (Compound 17 of Published Unexamined European Patent Apllication No. 354,532)

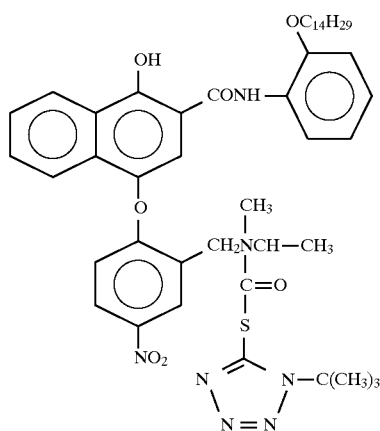

C-6 (Coupler 24 of Published Unexamined European Patent Application No. 89,834)

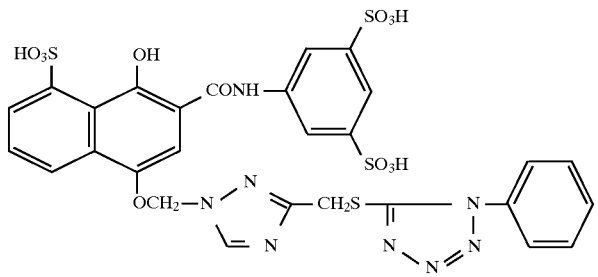

TABLE 3

|  | Average AgI content (%) | Average grain size (μm) | Variation coefficient (%) according to grain size | Diameter/ thickness ratio | Silver amount ratio (AgI content, %) |
|---|---|---|---|---|---|
| Emulsion A | 4.0 | 0.45 | 27 | 1 | Core/shell = 1/3(13/1), Double structure grain |
| Emulsion B | 8.9 | 0.70 | 16 | 6 | Core/shell = 3/7(25/2), Double structure grain |
| Emulsion C | 10 | 0.75 | 30 | 2 | Core/shell = 1/2(24/3), Double structure grain |
| Emulsion D | 16 | 0.85 | 17 | 7 | Core/shell = 4/6(40/0), Double structure grain |
| Emulsion E | 10 | 0.85 | 20 | 1 | Core/shell = 1/2(24/3), |

TABLE 3-continued

| | Average AgI content (%) | Average grain size (μm) | Variation coefficient (%) according to grain size | Diameter/ thickness ratio | Silver amount ratio (AgI content, %) |
|---|---|---|---|---|---|
| Emulsion F | 4.0 | 0.25 | 28 | 1 | Double structure grain Core/shell = 1/3(13/1), |
| Emulsion G | 14.0 | 0.75 | 25 | 2 | Double structure grain Core/shell = 1/2(42/0), |
| Emulsion H | 14.5 | 1.10 | 15 | 5 | Double structure grain Core/shell = 37/63(34/3), |
| Emulsion I | 1 | 0.07 | 15 | 1 | Double structure grain Uniform grain |

What is claimed is:

1. A silver halide color photographic photosensitive material in which at least one silver halide emulsion layer is formed on a support, wherein said material contains a compound represented by general formula (I) below in at least one layer:

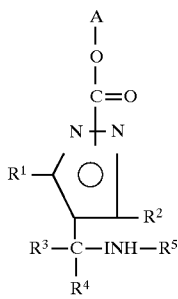

General Formula (I)

where A represents a coupler moiety, each of $R^1$ and $R^2$ independently represents a hydrogen atom or a substituent, each of $R^3$ and $R^4$ independently represents a hydrogen atom or an alkyl group, INH represents a group having a development inhibiting function, and $R^5$ represents a nonsubstituted phenyl group, a nonsubstituted primary alkyl group, or a primary alkyl group substituted with a group other than an aryl group, at least one of $R^1$ to $R^4$ being a substituent other than a hydrogen atom, and an —OC(=O)— group combining with one of two nitrogen atoms forming a pyrazole ring.

2. The material according to claim 1, wherein said material contains a compound represented by general formula (I) in which $R^3$ and $R^4$ are hydrogen atoms.

3. The material according to claim 1, wherein said material contains a compound represented by general formula (I) in which the sum of chemical formula weights of groups represented by $R^1$ and $R^2$ is less than 120.

4. The material according to claim 1, wherein the total amount of the compound of general formula (I) in the material is from $3\times10^{-7}$ to $1\times10^{-3}$ mol/m$^2$.

5. The material according to claim 4, wherein the total amount of the compound of general formula (I) in the material is from $3\times10^{-6}$ to $5\times10^{-4}$ mol/m$^2$.

6. The material according to claim 5, wherein the total amount of the compound of general formula (I) in the material is from $1\times10^{-5}$ to $2\times10^{-4}$ mol/m$^2$.

7. The material according to claim 1, wherein both of $R^1$ and $R^2$ are methyl.

8. The material according to claim 1, wherein said material contains a compound represented by general formula (I) in which a group represented by INH is one of (INH-1) to (INH-13) below:

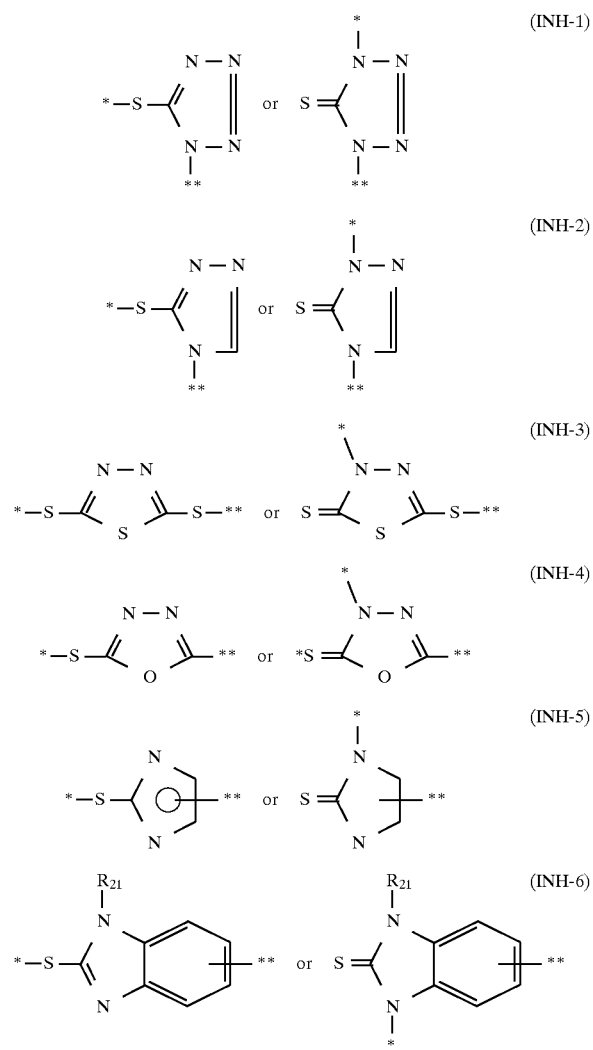

wherein $R_{21}$ represents a hydrogen atom or a substituted or unsubstituted hydrocarbon group,

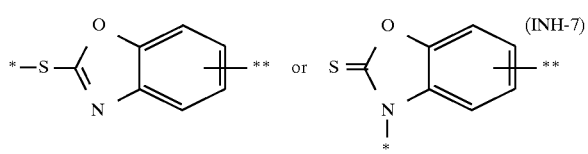

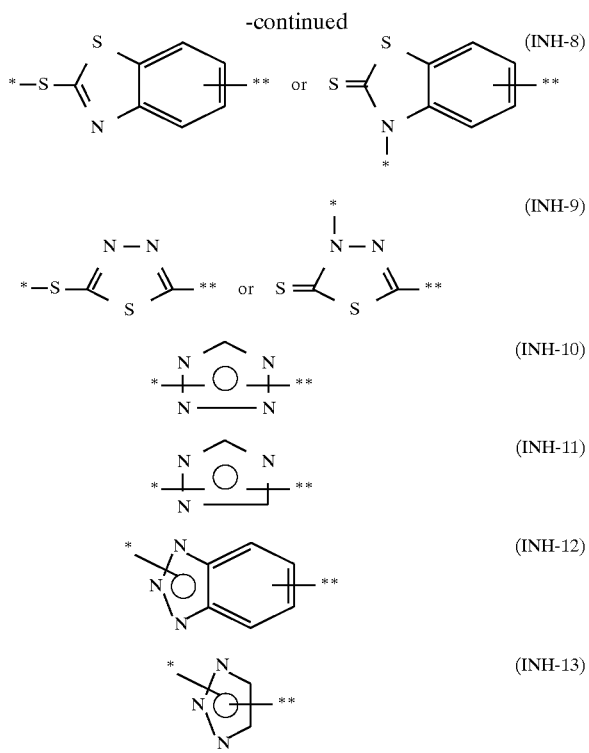

(wherein symbol * represents a position where the group is bonded with a group represented by —CR₃(R₄)— in the compound represented by general formula (I), and symbol ** represents a position where the group is bonded with R⁵).

9. The material according to claim 8, wherein said group represented by INH is one of (INH-1), (INH-2), (INH-3), (INH-4), (INH-9), and (INH-12).

10. The material according to claim 9, wherein said group represented by INH is (INH-1).

11. The material according to claim 1, wherein said material contains a compound represented by general formula (I) in which a group represented by $R^5$ is a phenyl group, a nonsubstituted primary alkyl group having 2 to 6 carbon atoms, or a primary alkyl group substituted with fluoro, chloro, an alkoxyl group, a carbamoyl group, an alkoxycarbonyl group, a cyano group, a nitro group, or —CO₂CH₂CO₂R₇₀ where $R_{70}$ represents a nonsubstituted alkyl group having 3 to 6 carbon atoms.

12. The material according to claim 11, wherein said group represented by $R^5$ is a nonsubstituted primary alkyl group or a primary alkyl group substituted with an alkoxycarbonyl group.

13. The material according to claim 12, wherein said group represented by $R^5$ is a nonsubstituted primary alkyl group having 3 to 5 carbon atoms.

14. The material according to claim 12, wherein said group represented by $R^5$ is a primary alkyl group substituted with an alkoxycarbonyl group.

15. The material according to claim 1, wherein said material contains a compound represented by general formula (I) in which both of groups represented by $R^1$ and $R^2$ are methyl, both of groups represented by $R^3$ and $R^4$ are hydrogen atoms, and $R^5$ is a nonsubstituted primary alkyl group having 3 to 5 carbon atoms or a primary alkyl group substituted with an alkoxycarbonyl group.

* * * * *